(12) United States Patent
He et al.

(10) Patent No.: US 9,018,377 B2
(45) Date of Patent: Apr. 28, 2015

(54) HYDROGEN PEROXIDE SENSORS BASED UPON PHOTO-INDUCED ELECTRON TRANSFER

(75) Inventors: Huarui He, Alpharetta, GA (US); Chao Lin, San Diego, CA (US)

(73) Assignee: OPTI Medical Systems, Westbrook, ME (US)

( * ) Notice: Subject to any disclaimer, the term of this patent is extended or adjusted under 35 U.S.C. 154(b) by 392 days.

(21) Appl. No.: 13/386,021

(22) PCT Filed: Jul. 22, 2010

(86) PCT No.: PCT/US2010/042910
§ 371 (c)(1),
(2), (4) Date: Mar. 30, 2012

(87) PCT Pub. No.: WO2011/011605
PCT Pub. Date: Jan. 27, 2011

(65) Prior Publication Data
US 2012/0183984 A1    Jul. 19, 2012

Related U.S. Application Data

(60) Provisional application No. 61/227,699, filed on Jul. 22, 2009.

(51) Int. Cl.
| | | |
|---|---|---|
| A61K 31/44 | (2006.01) |
| C07D 221/04 | (2006.01) |
| C07D 471/06 | (2006.01) |
| C07D 471/16 | (2006.01) |
| C07D 221/14 | (2006.01) |
| C07D 401/12 | (2006.01) |

(52) U.S. Cl.
CPC ...... *C07D 221/14* (2013.01); *Y10T 436/206664* (2015.01); *C07D 401/12* (2013.01)

(58) Field of Classification Search
None
See application file for complete search history.

(56) References Cited

U.S. PATENT DOCUMENTS

| | | | | |
|---|---|---|---|---|
| 3,096,333 | A * | 7/1963 | Wilson et al. | 546/100 |
| 6,171,866 | B1 * | 1/2001 | He et al. | 436/79 |
| 2006/0121623 | A1 * | 6/2006 | He et al. | 436/163 |

OTHER PUBLICATIONS

Qian, X. et al. Two regioisomeric and exclusively selective Hg(II) sensor molecules composed of a naphthalimide fluorophore and an o-phenylenediamine derived triamide receptor. Chem Comm. 2006, p. 109.*
Carey, FA. Organic Chemistry 6th Ed. McGraw Hill. 2006, chapter 1, p. 9.*
Pereyaslova, DG. et al. (Arylvinyl)-N-phenylnaphthalimides. USSR Zhurnal Prikladnoi Spektroskopii. 1982, vol. 37, p. 494.*
Bojinov, VB. et al. Synthesis and photophysical properties of fluorescence sensing ester- and amidoamine-functionalized 1,8-naphthalimides. Journal of Photochemistry A: Chemistry. 2008, vol. 193, p. 134.*
Wojciechowski, K. et al. Structure-property relationships in Azo Disperse Dyes, Derivatives of Naphthalimide. Dyes and Pigments. 1997, vol. 33, p. 161.*
Albers A., et al. "A Fret-Based Approach to Ratiometric Fluorescence Detection of Hydrogen Peroxide," J. Am. Chem. Soc. 128 (2006) 9640-9641.
Miller E.W., et al., "A Flourescent Sensor for Imaging Reversible Redox Cycles in Living Cells," J. Am. Chem. Soc. 129(2007) 3458-3459.
Soh N., et al., "Design and Development of a Fluorescent Probe for Monitoring Hydrogen Peroxide Using Photoinduced Electron Transfer," Bioorganic & Medicinal Chemistry 13(4) (2005) 1131-1139.
Soh N., et al., "Novel Fluorescent Probe for Detecting Hydroperoxides with Strong Emission in the Visible Range," Bioorganic & Medicinal Chemistry 16(11) (2006) 2943-2946.
Soh N., et al., "Swallow-tailed Perylene Derivative: a New Tool for Fluorescent Imaging of Lipid Hydroperxides," Org. Biomol. Chem. 5(2007) 3762-3768.
Srikun D. et al., "An ICT-Based Approach to Ratiometric Fluorescence Imaging of Hydrogen Peroxide Produced in Living Cells," J. Am. Chem. Soc. 130 (2008) 4596-4597.
Bojinov, et al., "Synthesis and Photophysical properties of fluorescence sensing ester- and amidoamine-functionalized 1,8-naphthalimides," Journal of Photchemistry and Photobiology A: Chemistry 193 (2008) 129-138.
Search Report in International Application PCT/US2010/042910 mailed Nov. 18, 2010.

* cited by examiner

*Primary Examiner* — Rita Desai
*Assistant Examiner* — Ben S Michelson
(74) *Attorney, Agent, or Firm* — Gilberto M. Villacorta; Yogeeta B. Jadhav; Foley & Lardner LLP

(57) ABSTRACT

The invention provides compounds of formula I F-L-Q (I) where F comprises a fluorophore capable of absorbing energy at an excitation wavelength and, in the absence of a quencher, emitting energy at an emission wavelength, which is different than the excitation wavelength; Q comprises a quencher; L comprises a linker moiety having two ends, one end being covalently bound to F and the other end being covalently bound to Q. The compounds are capable of undergoing a reversible reaction (1), provided below: (1) where $Q^+$ is an oxidized form of Q representing the absence of a quencher, Ox comprises an oxidizing agent, which is capable of oxidizing Q to its oxidized form Q, and Red comprises a reducing agent, which is capable of converting Q back to its reduced form Q. The compounds can undergo photo-induced electron transfer when irradiated with energy and when Q exists in its oxidized form, $Q^+$. The invention also provides methods of detecting and determining the presence of analytes and/or hydrogen peroxide in a sample, as well as a substrate that comprises the compound of formula I.

9 Claims, 8 Drawing Sheets

HYDROGEN PEROXIDE SENSORS BASED UPON PHOTO-INDUCED ELECTRON TRANSFER

BACKGROUND OF THE INVENTION

The present invention relates generally to the field of analytical chemistry and, more specifically, to practical applications of compounds that support photo-induced electron transfer.

Partially reduced reactive oxygen species (ROS) are prevalent in living systems. For instance, such species are implicated in a variety of biological mechanisms, such as the by-products of reactions between oxidative enzymes and their substrates. Hydrogen peroxide ($H_2O_2$) is an archetypal ROS and, hence, it is an attractive candidate for chemical probes of biological processes and, in general, for analytical applications where $H_2O_2$ may be generated.

Accordingly, traditional probes are designed to be sensitive to reduction-oxidation (redox) activity that is directly or indirectly related to hydrogen peroxide. For instance, probes in this regard typically include fluorophores that, only when oxidized, are amenable to straightforward detection by fluorescence. Whilst structurally diverse small molecules are suitable for this purpose in various degrees, a number of challenges present themselves regardless of the molecular scaffold of the probes. These challenges include, for instance, poor water solubility or incompatibility with water; the presence of moieties on a probe that can undergo side reactions with thiols, such as in cellular contexts; a need for external activating enzymes; and lack of membrane permeability.

Further, many traditional probes undergo irreversible oxidation and, accordingly, they can be used only once. Hence, such probes are incapable of reversibly responding to oxidation and reduction events. See N. Soh et al. "Design and Development of a Fluorescent Probe for Monitoring Hydrogen Peroxide Using Photoinduced Electron Transfer," *Bioorganic & Medicinal Chemistry* 13(4) (2005) 1131-1139; N. Soh et al. "Novel Fluorescent Probe for Detecting Hydroperoxides With Strong Emission in the Visible Range," *Bioorganic & Medicinal Chemistry* 16(11) (2006) 2943-2946; and N. Soh et al. "Swallow-tailed Perylene Derivative: a New Tool for Fluorescent Imaging of Lipid Hydroperoxides," *Org. Biomol. Chem.* 5 (2007) 3762-3768.

In general, fluorescent probes can operate via a range of energy transfer mechanisms. For instance, some probes are based upon irreversible processes utilizing Förster resonance energy transfer (FRET), also known as fluorescence resonance energy transfer, which is a mechanism describing energy transfer between two chromophores. See A. Albers et al. "A FRET-Based Approach to Ratiometric Fluorescence Detection of Hydrogen Peroxide," *J. Am. Chem. Soc.* 128 (2006) 9640-9641. Other fluorescent probes operate via an internal charge transfer (ICT) mechanism triggered, for instance, by an irreversible oxidation of the probe upon exposure to hydrogen peroxide. See D. Srikun et al. "An ICT-Based Approach to Ratiometric Fluorescence Imaging of Hydrogen Peroxide Produced in Living Cells," *J. Am. Chem. Soc.* 130 (2008) 4596-4597.

The inventors are aware of recent evidence of a fluorescent probe that incorporates a disulfide moiety and that is capable of achieving reversible fluorescence responses to hydrogen peroxide. See E. W. Miller et al. "A Fluorescent Sensor for Imaging Reversible Redox Cycles in Living Cells," *J. Am. Chem. Soc.* 129 (2007) 3458-3459. The probe in this instance is based upon internal charge transfer occurring within a single chromophore, like some of the irreversible fluorescent probes discussed above, not by simple photoinduced electron-transfer (PET).

There remains a need for efficient fluorescent probes that overcome traditional challenges to such probes, that are capable of responding reversibly to redox events, and that eliminate the presence of or need for chromophores that are operative in probes based upon ICT.

SUMMARY OF THE INVENTION

The present invention satisfies these needs and others by providing in one embodiment a compound having a chemical structure conforming to formula (I) below, or a salt thereof:

$$\text{F-L-Q} \tag{I}$$

In Formula I, F comprises a fluorophore that is capable of absorbing energy at an excitation wavelength and, in the absence of a quencher, emitting energy at an emission wavelength, which is different than the excitation wavelength. Moiety Q comprises a quencher, whilst L comprises a linker moiety having two ends, one end being covalently bound to F and the other end being covalently bound to Q. The compound of formula I is capable of undergoing a reversible reaction (1), provided below:

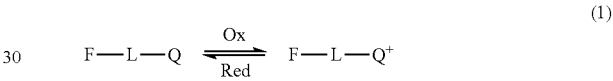

(1)

In reaction 1, $Q^+$ is an oxidized form of Q representing the absence of a quencher, Ox comprises an oxidizing agent, which is capable of oxidizing Q to its oxidized form $Q^+$, and Red comprises a reducing agent, which is capable of converting $Q^+$ back to its reduced form Q.

In another embodiment, the invention provides a method of determining a concentration of an analyte in a sample. The method comprises (a) contacting a sample suspected of containing an analyte with (i) a sufficient amount of a compound having a chemical structure conforming to formula (I) as described above wherein Red is substantially absent in the sample, and (ii) a sufficient amount of one or more reagents capable of reacting with or transforming the analyte, which reaction or transformation produces hydrogen peroxide in an amount that is proportional to the concentration of the analyte in the sample. The method further comprises (b) irradiating the sample with energy in the form of electromagnetic radiation, including energy at the excitation wavelength; (c) measuring an intensity of energy emitted from the irradiated sample at the emission wavelength, if any; and (d) correlating the measured intensity of the emitted energy with a concentration of the analyte in the sample.

In yet another embodiment, the invention provides a substrate that is useful in the detection of an analyte in a sample comprising a surface to which is affixed (i) an analytically effective amount of a compound having a chemical structure conforming to formula (I) as described above. The substrate further comprises on the surface (ii) a sufficient amount of one or more reagents capable of reacting with or transforming the analyte, which reaction or transformation produces hydrogen peroxide in an amount that is proportional to the concentration of the analyte in the sample.

Another embodiment of the invention is a method of determining a concentration of hydrogen peroxide in a sample. The method comprises (a) contacting a sample suspected of containing hydrogen peroxide ($H_2O_2$) with a sufficient amount of a compound having a chemical structure conforming to formula (I) as described above, wherein Red is substantially absent in the sample; (b) irradiating the sample with energy in the form of electromagnetic radiation, including energy at an excitation wavelength at which the fluorophore absorbs the energy; (c) measuring an intensity of energy emitted from the irradiated sample at an emission wavelength, if any; and (d) correlating the measured intensity of the emitted energy with a concentration of the hydrogen peroxide in the sample.

The invention also provides, in another embodiment, a method of detecting the presence of hydrogen peroxide in a sample comprising (a) contacting a sample suspected of containing hydrogen peroxide with a sufficient amount of a compound having a chemical structure conforming to formula (I) as described above, wherein Red is substantially absent in the sample. The method further comprises (b) irradiating the sample with energy in the form of electromagnetic radiation, including energy at an excitation wavelength at which the fluorophore absorbs the energy; and (c) detecting energy emitted from the irradiated sample at an emission wavelength, if any. The detection of emitted energy in step (c) supports a conclusion that at least some hydrogen peroxide is present in the sample.

DETAILED DESCRIPTION

Definitions

Figure 1:
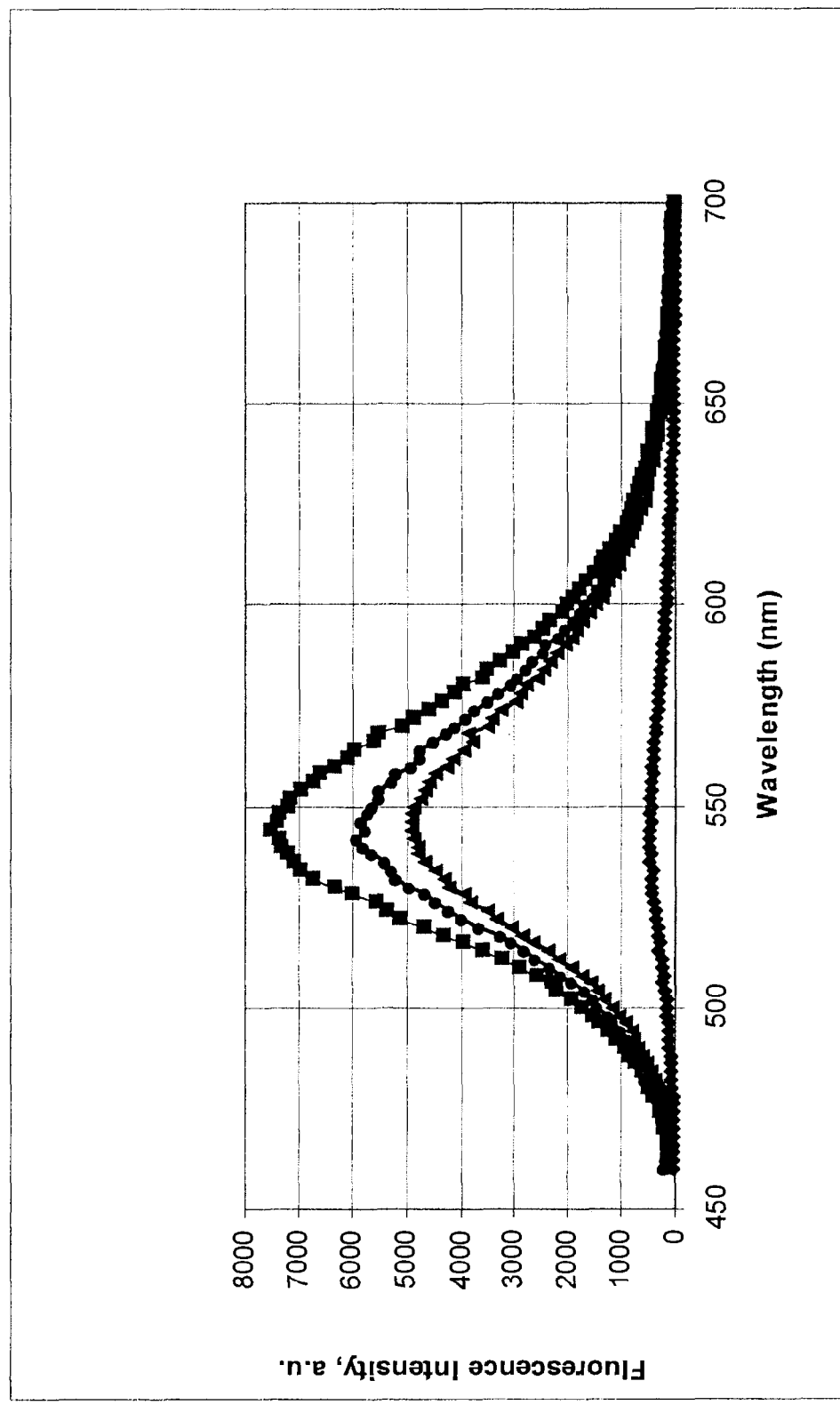
FIG. 1 is a stacked plot of fluorescence emission intensity (arbitrary units "a.u.") versus wavelength for aqueous solutions of Compound A salt (100 μM) in 2.5 ml pH Tris buffer ("♦"), after addition of 20 μl horse radish peroxidase (HRP; 2500 unit/ml; also "♦"), and then after addition of a 20 μL aliquot of 5 mM hydrogen peroxide at the intervals of 0 minutes ("▲"), 1 minute ("●"), and 2 minutes ("■").

The term "aryl" in the present description is intended to include aromatic rings (monocyclic or bicyclic) having from 6 to 10 ring carbon atoms, such as phenyl (Ph), naphthyl, and indanyl (i.e., 2,3-dihydroindenyl), which optionally may be substituted by $C_{1-6}$-alkyl. Examples of substituted aryl groups are benzyl, and 2-methylphenyl.

The term "heteroaryl" means in the present description a monocyclic, bi- or tricyclic aromatic ring system (only one ring need to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen and selenium as part of the ring system. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, quinoline, quinoxaline, isoquinoline, phthalazine, cinnoline, quinazoline, indole, isoindole, benzothiophene, benzofuran, isobenzofuran, benzoxazole, 2,1,3-benzoxadiazole, benzopyrazole; benzothiazole, 2,1,3-benzothiazole, 2,1,3-benzoselenadiazole, benzimidazole, indazole, benzodioxane, indane, 1,5-naphthyridine, 1,8-naphthyridine, acridine, fenazine and xanthene.

The term $C_{1-8}$-alkyl in the compound of formula (I) according to the present application can be a straight or branched alkyl group containing 1-8 carbon atoms. Exemplary alkyl groups include methyl, ethyl, n-propyl, isopropyl, n-butyl, sec-butyl, tert-butyl, pentyl, isopentyl, hexyl, isohexyl, n-heptyl, and n-octyl. For parts of the range "$C_{1-8}$-alkyl" all subgroups thereof are contemplated such as $C_{1-7}$-alkyl, $C_{1-6}$-alkyl, $C_{1-5}$-alkyl, $C_{1-4}$-alkyl, $C_{2-8}$-alkyl, $C_{2-7}$-alkyl, $C_{2-6}$-alkyl, $C_{2-5}$-alkyl, $C_{4-6}$-alkyl, etc.

The term $C_{1-8}$-alkoxy in the compound of formula (I) according to the present application can be a straight or branched alkoxy group containing 1-8 carbon atoms. Exemplary alkoxy groups include methoxy, ethoxy, propoxy, isopropoxy, butoxy, sec-butoxy, tert-butoxy, pentyloxy, isopentyloxy, hexyloxy, isohexyloxy, n-heptyloxy, and n-octyloxy. For parts of the range "$C_{1-6}$-alkoxy" all subgroups thereof are contemplated such as $C_{1-7}$-alkoxy, $C_{1-6}$-alkoxy, $C_{1-5}$-alkoxy, $C_{1-4}$-alkoxy, $C_{2-8}$-alkoxy, $C_{2-7}$-alkoxy, $C_{2-6}$-alkoxy, $C_{2-5}$-alkoxy, $C_{3-7}$-alkoxy, $C_{4-6}$-alkoxy, etc.

The term $C_{2-8}$-alkenyl in the compound of formula (I) according to the present application may be a straight or branched alkenyl group containing 2-8 carbon atoms. Exemplary alkenyl groups include vinyl, 1-propenyl, 2-propenyl, isopropenyl, 1-butenyl, 2-butenyl, 1-pentenyl, 2-pentenyl, 1-hexenyl, 2-hexenyl, 1-heptenyl, and 1-octenyl. For parts of the range "$C_{2-8}$-alkenyl" all subgroups thereof are contemplated such as $C_{2-7}$-alkenyl, $C_{2-6}$-alkenyl, $C_{2-5}$-alkenyl, $C_{2-4}$-alkenyl, $C_{3-8}$-alkenyl, $C_{3-7}$-alkenyl, $C_{3-6}$-alkenyl, $C_{3-5}$-alkenyl, $C_{4-7}$-alkenyl, $C_{5-6}$-alkenyl, etc.

The term "$C_2$-$C_8$ alkynyl" as used herein refers to a straight or branched chain unsaturated hydrocarbon containing 2-8 carbon atoms and at least one triple bond. Examples of a $C_2$-$C_8$ alkynyl group include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne, isohexyne, 1-heptyne, 2-heptyne, 3-heptyne, isoheptyne, 1-octyne, 2-octyne, 3-octyne, 4-octyne, and isooctyne.

The term $C_{3-10}$-cycloalkyl in the compound of formula (I) according to the present application can be an optionally substituted monocyclic, bicyclic or tricyclic alkyl group containing between 3-10 carbon atoms. Exemplary cycloalkyl groups include cyclopropyl, cyclobutyl, cyclopentyl, cyclohexyl, cycloheptyl, cyclooctyl, cyclononyl, cyclodecyl, bicyclo[2.2.1]hept-2-yl, tricyclo[3.3.1.0~3,7~]non-3-yl, (1R,2R,3R,5S)-2,6,6-trimethylbicyclo[3.1.1]hept-3-yl, (1S,2S,3S,5R)-2,6,6-trimethylbicyclo[3.1.1]hept-3-yl, 1-adamantyl, noradamantyl, and 2,2,3,3-tetramethylcyclopropyl. For parts of the range "$C_{3-10}$-cycloalkyl" all subgroups thereof are contemplated such as $C_{3-9}$-cycloalkyl, $C_{3-8}$-cycloalkyl, $C_{3-7}$-cycloalkyl, $C_{3-6}$-cycloalkyl, $C_{3-5}$-cycloalkyl, $C_{4-10}$-cycloalkyl, $C_{5-10}$-cycloalkyl, $C_{6-10}$-cycloalkyl, $C_{7-10}$-cycloalkyl, $C_{8-9}$-cycloalkyl, etc. In addition, the cycloalkyl moiety may optionally be substituted with one or more oxo groups.

As used herein, the term "heterocycle" as used herein refers to 5- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles generally include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl.

The term "hydroxyalkyl," as used herein, refers to a $C_1$-$C_8$ alkyl group in which one or more of the $C_1$-$C_6$ alkyl group's hydrogen atom is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, and CH$_2$CH$_2$CH$_2$CH$_2$CH$_2$CH$_2$OH.

The term "halo" as used herein refers to —F, —Cl, —Br or —I.

The term "haloalkyl," as used herein, refers to a $C_1$-$C_8$ alkyl group wherein from one or more of the $C_1$-$C_8$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

As used herein, the term "heteroatom" is meant to include oxygen (O), nitrogen (N), and sulfur (S).

Depending on the structure of the compound of formula I, the term "salt," as used herein, refers to an organic or inorganic acid or base salt of the compound. Representative salts include, for instance, alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methyl sulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a salt can have more than one charged atom in its structure. In this instance the salt can have multiple counterions. Hence, a salt can have one or more charged atoms and/or one or more counterions.

Compounds

In some embodiments, quencher Q in the compound of formula I is capable of absorbing energy from fluorophore F via a photo-induced electron transfer (PET) quenching mechanism in the absence of an oxidizing agent Ox. Upon exposure to an oxidizing agent, however, Q is oxidized to $Q^+$, representing the absence of a quencher, thereby rendering Q incapable of absorbing energy from F via a PET quenching mechanism.

Typical fluorophores F are described below in relation to formula Ia. Suitable examples of F also include polycyclic aromatic hydrocarbons (PAHs) as summarized in following Table 1. In these examples, a linker L in formula I can be bonded to any suitable point of attachment on fluorophore F. For clarity, Table 1 depicts only the core structure of exemplary fluorophores F, but they can be substituted independently by 1-3 R' as defined below.

TABLE 1

Examples of Polycyclic Aromatic Hydrocarbons as Fluorophores

Two Ring

 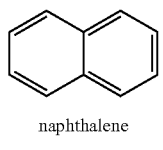

azulene          naphthalene

Three Ring

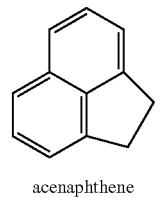 [SMILES: c1cc2c3c(cccc3c1)CC2] 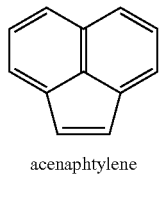 [SMILES: C1=Cc2cccc3cccc1c23]

acenaphthene          acenaphtylene

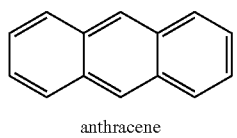 [SMILES: c1ccc2cc3ccccc3cc2c1] 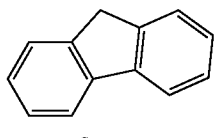

anthracene          fluorene

TABLE 1-continued
Examples of Polycyclic Aromatic Hydrocarbons as Fluorophores
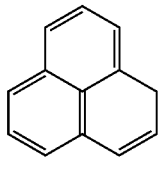
phenalene
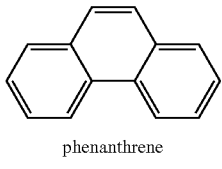 [SMILES: c1ccc2c(c1)ccc1ccccc12]
phenanthrene
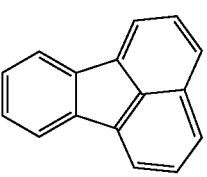
fluoranthene
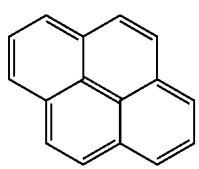
pyrene
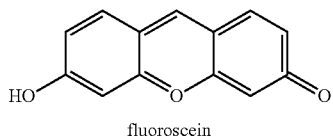
fluoroscein
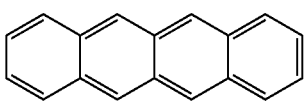
tetracene
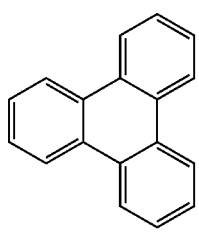
triphenylene
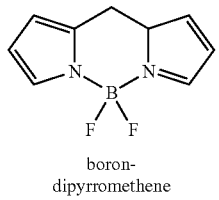
boron-dipyrromethene
Four Ring
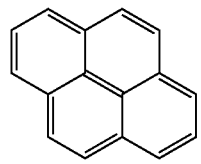
pyrene
Five+ Ring
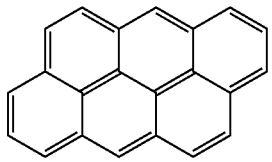
dibenzo[def,mno]chrysene
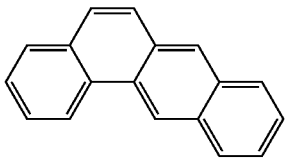
benzo[a]anthracene
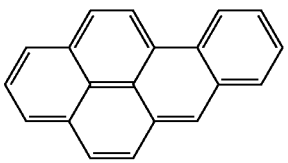
benzopyrene
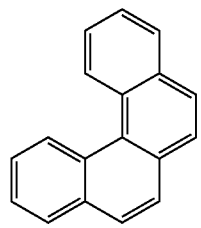
benzo[c]anthracene
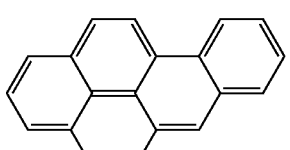
benzo[a]pyrene
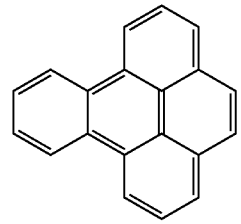
benzo[e]pyrene
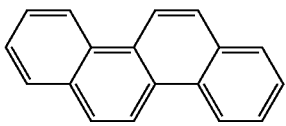
chrysene
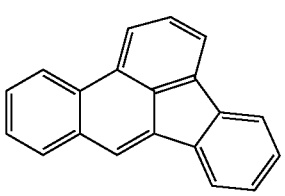
benzo[b]fluoranthene TABLE 1-continued Examples of Polycyclic Aromatic Hydrocarbons as Fluorophores

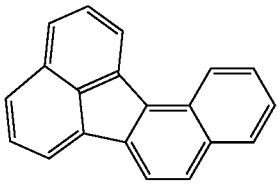

benzo[i]fluoranthene

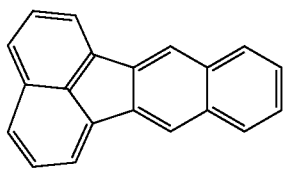

benzo[k]fluoranthene

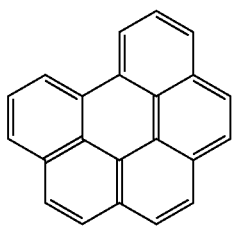

benzo[ghi]perylene

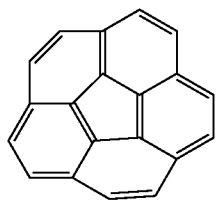

Dibenzo[ghi,mno]fluoranthene

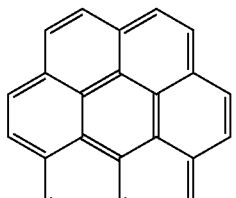

coronene

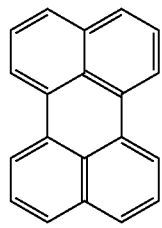

perylene

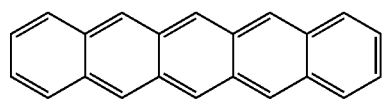

pentacene

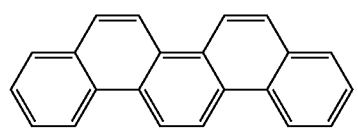

TABLE 1-continued

Examples of Polycyclic Aromatic Hydrocarbons as Fluorophores

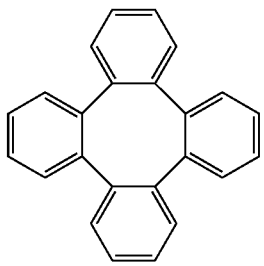

tetraphenylene

In other embodiments, quencher Q comprises a five- or six-membered aryl or heteroaryl group that is substituted by at least one substituent selected from the group consisting of $OR^1$, $SR^1$, and $N(R^1)_2$. In these embodiments, each instance of $R^1$ can be hydrogen or $C_{1-6}$-alkyl, selected independently. Specific examples of quencher Q include but are not limited to the following moieties, which can be attached to linker L at any suitable point of attachment, such as any available ring carbon:

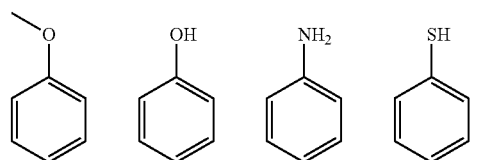

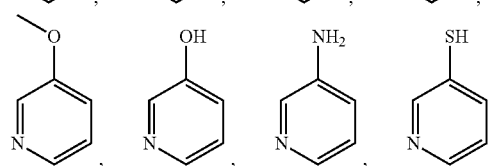

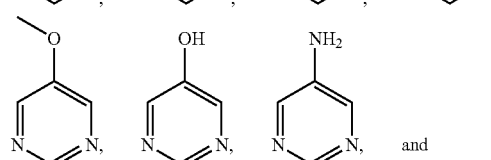

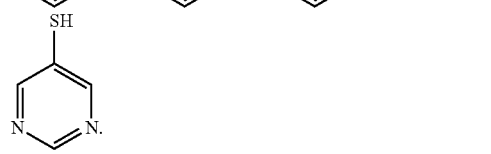

In still other embodiments, linker L in formula I comprises a saturated or unsaturated, linear or branched aliphatic chain including 1-6 carbon atoms. For instance, in some embodiments 1-3 carbon atoms in L are optionally and independently replaced by $NR^1$—, —O—, or —S—, wherein $R^1$ is hydrogen or $C_{1-6}$-alkyl. Specific examples of L include but are not limited to the following:

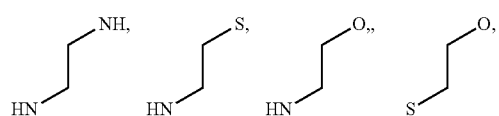

-continued

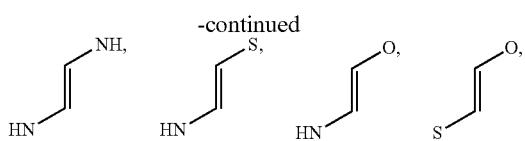

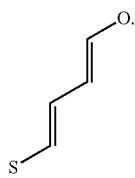

In yet other embodiments, the compound of formula I has a chemical structure that conforms to formula IA, as shown below:

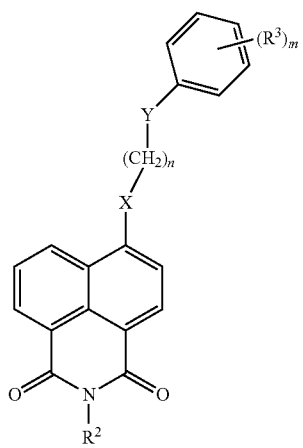

IA

In formula IA, $R^2$ is selected from the group consisting of H, aryl, aryloxy, heteroaryl, heteroaryloxy, $C_{1-8}$-alkyl, $C_{1-8}$-alkoxy, $C_{1-8}$-alkyl-aryl, $C_{1-8}$-alkyl-heteroaryl, $C_{1-8}$-alkyl-$C_{1-8}$-alkoxy, $C_3$-$C_{10}$-cycloalkyl, $C_3$-$C_{10}$-heterocycloalkyl, N(R')$_2$, —C(O)N(R)$_2$, —N(R')C(O)OR'; wherein any alkyl, cycloalkyl, heterocycloalkyl, aryl, or heteroaryl is optionally substituted with from one to four substituents selected from the group consisting of oxo, halogen, —CN, —NO$_2$, $C_{2-8}$-alkenyl, $C_{2-8}$-alkynyl, $C_{1-8}$-alkoxy, $C_{1-8}$-haloalkyl, $C_{1-8}$-hydroxyalkyl, aryloxy, heteroaryl, —C(O)R', —C(O)OR', —NR'C(O)OR", —OR', —SR', —OC(O)R', —C(O)N(R')$_2$, —S(O)R", —SO$_2$R", —SO$_2$N(R')$_2$, —N(R')$_2$ and —NR'C(O)R'.

Each occurrence of R' is independently selected from the group consisting of H, $C_{1-8}$-alkyl, $C_{2-8}$-alkenyl, $C_{2-8}$-alkynyl, $C_{1-4}$-alkoxy, $C_{1-8}$-hydroxyalkyl, $C_{1-8}$-hydroxy-diaryl-alkyl, $C_{3-8}$-cycloalkyl, $C_{3-8}$-heterocycloalkyl, heteroaryl, aryl, $C_{3-8}$-cycloalkyl-$C_{1-6}$-alkyl, $C_{3-8}$-heterocycloalkyl-$C_{1-6}$-alkyl, heteroaryl-$C_{1-6}$-alkyl, and aryl-$C_{1-6}$-alkyl.

Each occurrence of R" is independently an unsubstituted moiety selected from the group consisting of $C_{1-8}$-alkyl, $C_{2-8}$-alkenyl, $C_{2-8}$-alkynyl, $C_{1-8}$-haloalkyl, $C_{1-8}$-hydroxyalkyl, $C_{3-8}$-cycloalkyl, $C_{3-8}$-heterocycloalkyl, heteroaryl, aryl, $C_{3-8}$-cycloalkyl-$C_{1-6}$-alkyl, $C_{3-8}$-heterocycloalkyl-$C_{1-6}$-alkyl, heteroaryl-$C_{1-6}$-alkyl, and aryl-$C_{1-6}$-alkyl.

Substituent $R^3$, in each instance, is independently selected from the group consisting of $OR^1$, $SR^1$, and $N(R^1)_2$.

$R^1$ is hydrogen or $C_{1-6}$-alkyl.

Variables X and Y are independently selected from group consisting of —NR$^1$—, —O—, and —S— Subscript m is 1, 2, 3, 4, or 5; and n is 1, 2, 3, 4, 5, or 6. When n is at least 2, then 2 and 4 hydrogen atoms in adjacent —CH$_2$— groups in —X—(CH$_2$)$_n$Y— are optionally not present so as to represent the moieties —CH=CH— and —C≡C—, respectively.

In some embodiments, substituent $R^2$ is selected from $C_{1-8}$-alkyl, $C_{1-8}$-alkoxy, $C_{1-8}$-alkyl-aryl, $C_{1-8}$-alkyl-heteroaryl, $C_{1-8}$-alkyl-$C_{1-8}$-alkoxy. In these embodiments, variables X and Y are independently selected from the group consisting of —NR$^1$— and —O—; m is 1 or 2; and n is 2 or 3.

In some embodiments, the compound does not contain a disulfide (i.e., —S—S—) moiety. In yet other embodiments, the compound does not contain a phosphine or phosphine oxide moiety.

Exemplary compounds of formulae I and IA include the following:

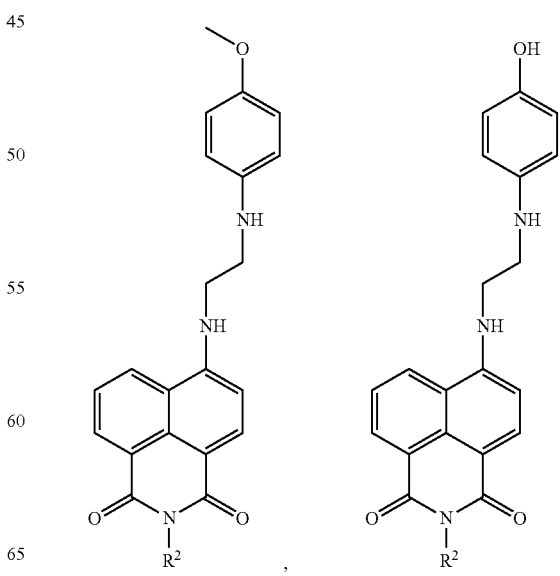

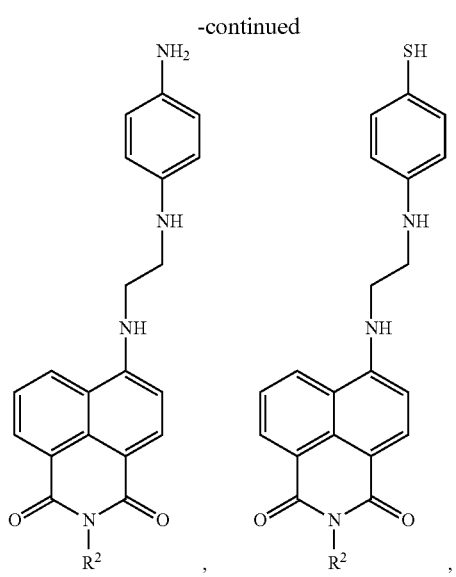

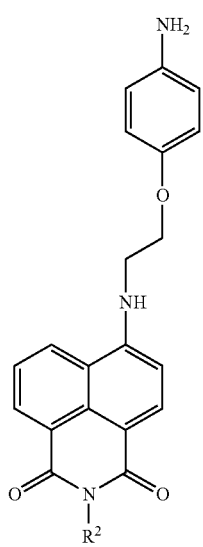

In one embodiment, the compound is:

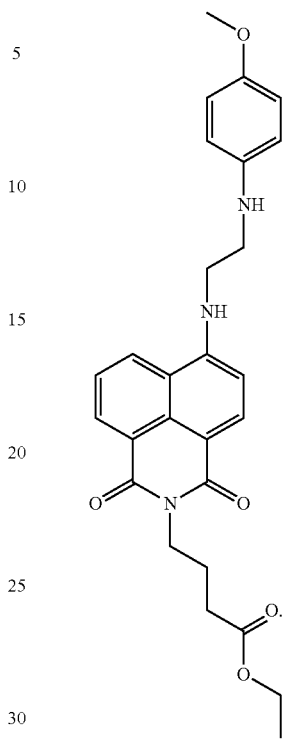

In other embodiments, the compound is:

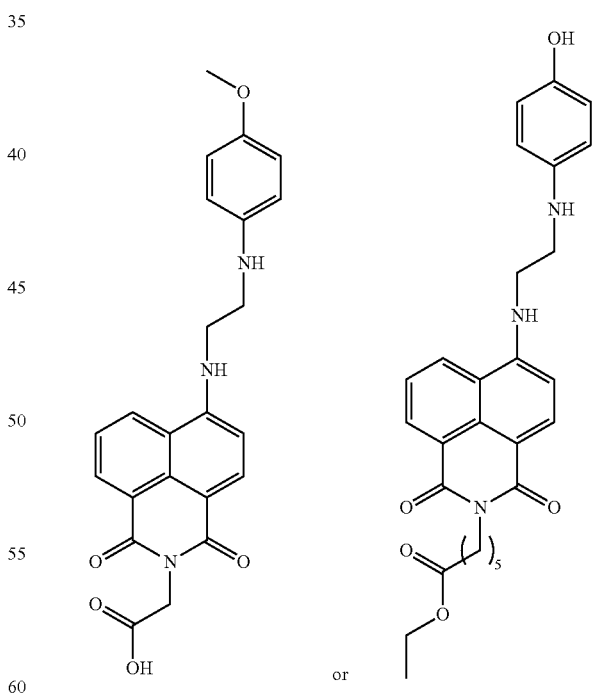

Any of the foregoing embodiments are suitable for use in combination with any other embodiment herein described, such as those of the methods and substrates described below.

Methods

The compounds of the present invention as provided in one embodiment are useful in a method of determining a concentration of an analyte in a sample as described above. In general, the method does not directly detect an analyte, but rather detects a concentration of hydrogen peroxide that is correlated directly with the concentration of the analyte. Thus, the method comprises contacting a sample suspected of containing the analyte with a compound of the invention and a sufficient amount of one or more reagents capable of reacting with or transforming the analyte so as to produce hydrogen peroxide in an amount that is proportional to the concentration of the analyte in the sample.

In general, any analyte is useful where its reaction with or transformation by one or more reagents produces hydrogen peroxide. For example, an analyte-reagent pair suitable for use in the method includes lactate and lactate oxidase and peroxidase. The known reaction between this analyte and reagents in the presence of oxygen produce pyruvate and hydrogen peroxide in known stoichiometric quantities. Another exemplary analyte is creatinine, the hydrolysis of which is catalyzed by creatinine amidohydrolase, and the creatine so produced is assayed in reactions catalyzed sequentially by creatine amidinohydrolase and sarcosine oxidase in a system that generates hydrogen peroxide.

A further example of an analyte is glucose. Because the reagents glucose oxidases (GOx) can specifically catalyze the oxidation of β-D-(+)-glucose to generate $H_2O_2$, the method of this invention is useful, for instance, in determining blood serum glucose concentrations. Thus, in general, other analytes can be chosen on the basis of their reactivity with oxidases—the reagents of the inventive method—to produce hydrogen peroxide.

Other analytes can include naturally occurring substances, artificial substances, metabolites, and/or reaction products. In some embodiments, the analyte is albumin, creatinine, glucose, hematocrit, lactate, lactate dehydrogenase, monoamines, cytochrome P450, cytochrome c, phosphorus, potassium, sodium, total protein, uric acid, metabolic markers, and drugs. However, other analytes are contemplated as well, including but not limited to acetaminophen, dopamine, ephedrine, terbutaline, ascorbate, uric acid, oxygen, d-amino acid, plasma amine, xanthine, NADPH, lysine, L-gulonolactone, alcohol, alcohol dehydrogenase, pyruvate dehydrogenase, diols, bilirubin, cholesterol, triglycerides, gentisic acid, ibuprophen, L-Dopa, methyl dopa, salicylates, tetracycline, tolazamide, tolbutamide, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-.beta. hydroxy-cholic acid; cortisol; creatine kinase; creatine kinase MM isoenzyme; cyclosporin A; d-penicillamine; de-ethylchloroquine; dehydroepiandrosterone sulfate; DNA, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, 21-deoxycortisol; desbutylhalofantrine; dihydropteridine reductase; diptheria/tetanus antitoxin; erythrocyte arginase; erythrocyte protoporphyrin; esterase D; fatty acids/acylglycines; free .beta.-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, .beta.); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae, Myoglobin, Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The sample from above then is understood to contain the compound of formula I wherein Q exists in its oxidized form $Q^+$ to the extent that any concentration of hydrogen peroxide has been generated. Accordingly, in one embodiment, $Q^+$ is able to photoquench, and so irradiating the sample with energy, such as by electromagnetic radiation, gives rise to photo-induced electron transfer (PET) from $Q^+$ to fluorophore F. In general, irradiation at any wavelength and intensity that gives rise to PET is desirable. Typical embodiments of the method employ optimized wavelengths—the excitation wavelength—that most efficiently stimulates PET. Methodologies and instrumentation for irradiating samples are well known in the art.

The irradiated sample then is monitored for intensity of any emitted energy at an emission wavelength, if any. Without wishing to be bound by any particular theory, the inventors believe that emitted energy can result from fluorescence attributed to F in its excited state, according to principles prescribed by the PET mechanism.

The intensity of any emitted energy then is measure by detectors or instrumentation well known in the analytical arts. The intensity therefore can be correlated with a concentration of analyte in the sample.

In another embodiment, the invention provides a method for determining a concentration of hydrogen peroxide in a sample as set forth in general terms hereinabove. In this embodiment, similar to the method described immediately above, a sample suspected of containing hydrogen peroxide is contacted with a compound formula I. Reaction between any hydrogen peroxide and the compound can result in the oxidation of Q to $Q^+$. In one embodiment, Q is capable of absorbing energy from F via a PET quenching mechanism, whereby oxidation of Q to $Q^+$ prevents operation of PET. The sample then is irradiated with energy as described above, such as at an excitation wavelength at which the fluorophore F absorbs energy. The intensity of any emitted energy at an emission wavelength is then measured and correlated with a concentration of hydrogen peroxide in the sample. In this manner, the method is suitable for quantitative determination of hydrogen peroxide.

In another embodiment, the invention provides a method that is useful, for instance, in the qualitative determination of the presence of hydrogen peroxide in a sample. Thus, a sample suspected of containing hydrogen peroxide is contacted with a compound formula I. Reaction between any hydrogen peroxide and the compound can result in the oxidation of Q to $Q^+$. In one embodiment, Q is capable of absorbing energy from F via a PET quenching mechanism, whereby oxidation of Q to $Q^+$ prevents operation of PET. The sample then is irradiated with energy as described above, such as at an excitation wavelength at which the fluorophore F absorbs energy. The intensity of any emitted energy at an emission wavelength is then detected. Any emitted energy that is detected supports a conclusion that at least some hydrogen peroxide is present in the sample. In some embodiments, the method further comprises measuring an intensity of the emitted energy at an emission wavelength.

Suitable samples for use in the methods of the invention include any that are suspected of containing an analyte or hydrogen peroxide. Typical samples are aqueous or primarily aqueous. For instance, the samples can include bodily fluids, such as blood, serum, plasma, interstitial fluid, cerebral spinal fluid, lymph fluid, ocular fluid, saliva, oral fluid, urine, excretions or exudates. Other samples include living cells and cell cultures.

The compound of formula I having Q in its oxidized form, $Q^+$, can be contacted with a reducing agent, Red, for conversion back to the compound containing Q, i.e., as its reduced form. In principle, any reducing agent is suitable for this purpose. In some embodiments, the reducing agents are mild enough so as to prevent chemical degradation of the compound of formula I. The reducing agent typically is compatible with the chemical environment in which the compound used as prescribed by the methods set forth herein. Many reducing agents are known in the art for this purpose. Exemplary reducing agents include but are not limited to thiols, thiosulfates, sulfite, sodium bisulfite, phosphines, vitamin C, iron (II) ion, oxalic acid, ascorbic acid, formic acid, and tris(2-carboxyethyl)-phosphate hydrochloride (TCEP).

Substrate

As summarized above, the invention also provides in another embodiment a substrate that is useful for the detection of an analyte in a sample. In general, the substrate comprises an analytically effective amount of a compound of formula (I) as set forth herein and a sufficient amount of one or more reagents capable of reacting with or transforming the analyte. The reaction or transformation produces hydrogen peroxide in an amount that is proportional to the concentration of the analyte in the sample.

Thus, in some embodiments, optionally in combination with any of the methods described above, the invention provides a method for determining the concentration of the analyte in the sample by contacting the sample with the substrate.

In some embodiments, the substrate is a film that is formed by coating onto a surface a solution comprising a compound of formula I, optionally in combination with one or more reagents that can transform or react with an analyte so as to produce hydrogen peroxide. In exemplary embodiments, the solution further comprises one or more agents that can be photocured, whereby the film is permanently affixed to the surface. Many such agents are known in the art and they are typically cured by exposure to heat and/or UV radiation. For instance, one or more types of reactive monomers can (co) polymerize upon conditions suitable for curing. In certain embodiments, the cured film thus constitutes a portion of the substrate and is useful for affixing one face of the film upon a surface of the substrate while exposing the opposing face of the film to samples for use in the methods described herein.

In some embodiments, the substrate comprises a metal, such as gold, aluminum, iron, titanium, chromium, platinum, copper and their respective alloys. Such metals can be derivatized on their surfaces with silicon dioxide, for instance, to provide reactive groups for linking. One method of derivatizing a metal surface is to sputter a metal oxide, such as silicon oxide, onto the metal surface.

Alternatively, the substrate can comprise silicon, glass or an organic polymer, such as a plastic. In certain embodiments, the substrate can be transparent.

In other embodiments, the film can be the substrate, itself. In any event the substrate can be incorporated into a sensor that is useful for detecting or quantifying the presence of hydrogen peroxide and/or the analytes described herein. The sensor may comprise a substrate layer (e.g., including a film layer), as set forth above. Illustrative embodiments further provide for the substrate layer to be affixed to a surface and optionally coated with a diffusion and/or optical isolation layer. The diffusion layer permits ingress of oxygen, hydrogen peroxide, and/or an analyte but regulates diffusion of the one or more reagents described above from the substrate. An optical isolation layer is not necessary but, if present, it can isolate the substrate from ambient light to reduce any contamination of energy at the emitted wavelength as described above. An illustrative material for the optical isolation layer is carbon black, which is useful for its optical properties as well and for its porosity. In some embodiments, the diffusion and optical isolation layers are simply combined into one layer.

The sensor is provided in any convenient physical form. For instance, in some embodiments, the layers described above, including the substrate layer, can be cut or punched into a variety of shapes and sizes. An illustrative embodiment of the sensor is a disc, which is formed in straightforward fashion by punching the formed layers with any readily available die known to those who are skilled in the art.

The invention is further described by the following examples, which are not intended to limit the scope of the invention, but rather are intended to illustrate certain embodiments.

EXAMPLE 1

Synthesis of Compound of Formula I

Scheme I below illustrates the overall synthesis of a compound of Formula I.

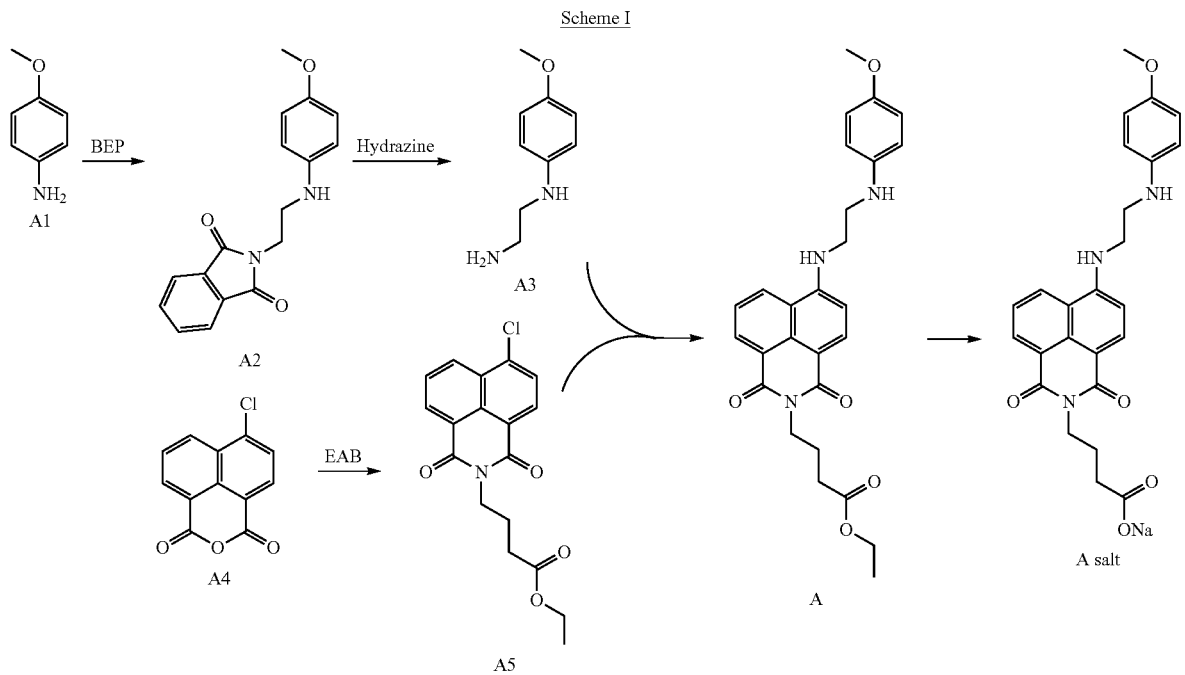

Scheme I

EXAMPLE 1A

Synthesis of A2

A suspension of 12.3 g (100 mmol) p-Anisidine (A1), 25.4 g (100 mmol) N-(2-bromoethyl)phthalimide, 13.8 g (100 mmol) $K_2CO_3$ and 50 ml DMF was heated at 90° C. for 20 h and then poured into 1 L ice water. After sitting for 2 h, the resulting precipitate was filtered, washed with water (3×200 ml), and dried at 60° C. for 24 h. The crude product was recrystallized from 800 ml ethanol to yield 24.3 g (82%) of A2 as an off-white powder. $H^1$NMR (300 MHz, $CDCl_3$) δ (ppm) 3.38 (t, 2H, $HNCH_2$), 3.68 (s, 3H, $OCH_3$), 3.93 (t, 2H, $C(O)NCH_2$), 6.56-6.76 (m, 4H, Methoxy-Ar—H), 7.65-7.83 (m, 4H, phthalimide-Ar—H).

EXAMPLE 1B

Synthesis of A3

23.4 g (78 mmol) of Compound A2 was dissolved in 430 ml boiling ethanol, and then 9.16 g (155 mmol) hydrazine hydrate was added in one portion. The solution boiled for 4 h. After cooling the solution, the solid was filtered off and washed with ethanol (2×100 ml). The solvent was evaporated off to afford 7.12 g of A3 as a light yellow oil, which was used directly in next step without further purification. $H^1$NMR (300 MHz, $CDCl_3$) δ (ppm) 2.00 (b, 2H, $NH_2$), 2.95 (t, 2H, $H_2NCH_2$), 3.18 (t, 2H, $HNCH_2$), 3.75 (s, 3H, $OCH_3$), 6.56-6.76 (m, 4H, Methoxy-Ar—H).

EXAMPLE 1C

Synthesis of A5

A suspension of 23.2 g (100 mmol) 4-chloro-1,8-naphthalic anhydride (A4), 18.4 g (110 mmol) ethyl 4-aminobutyrate, and 11.1 g (110 mmol) triethylamine in 300 ml DMF was stirred at room temperature for 18 h, and then at 80° C. for 1 h. The mixture was poured into 3 l water. The resulting precipitate was filtered and washed with water (2×100 ml). The wet crude product was dissolved in 400 ml boiling ethanol and hot filtered. The filtrate was left to cool for 4 h. The resulting crystals were filtered, washed with ethanol (2×20 ml), and dried at room temperature for 18 h to yield 25.2 g (73%) of A5 as a light yellow powder. $H^1$NMR (300 MHz, $CDCl_3$) δ (ppm) 1.25 (t, 3H, $CH_3$), 2.05 (m, 2H, $CH_2CH_2CH_2$), 2.45 (t, 2H, $C(O)CH_2$), 4.08 (q, 2H, $OCH_2$), 4.15 (t, 2H, $C(O)NCH_2$), 7.80-8.60 (m, 5H, Ar—H).

EXAMPLE 1D

Synthesis of A

A suspension of 6.40 g (38 mmol) Compound A3, 6.7 g (19 mmol) Compound A5, 2.49 g (19 mmol) diisopropylethylamine and 38 ml N-methyl-2-pyrrolidinone (NMP) was stirred at 90° C. for 18 h. The mixture was poured into 380 ml water. The resulting precipitate was centrifuged and the gummy solid was collected, then dissolved in $CH_2Cl_2$ (400 ml), washed with water (2×400 ml), and dried over $Na_2SO_4$. The solvent was evaporated to obtain 11.3 g of an oil, which was further purified by column chromatography to yield 4 g of oily crystals. After trituration of 20 ml ethanol, compound A was afforded as 3.4 g (19%) of yellow crystals. H¹NMR (300 MHz, CDCl₃) δ (ppm) 1.25 (t, 3H, CH₃), 2.05 (m, 2H, CH₂CH₂ CH₂), 2.40 (t, 2H, C(O)CH₂), 3.60 (m, 4H, HNCH₂CH₂NH 4.08 (q, 2H, OCH₂), 4.15 (t, 2H, C(O) NCH₂), 5.88 (s, 1H, NH), 6.60-6.90 (m, 5H, 4H for Methoxy-Ar—H, 1H for Naphthalene Ar—H), 7.80-8.60 (m, 4H, Ar—H).

EXAMPLE 1E

Synthesis of A Salt

A solution of 0.48 g (0.68 mmol) Compound A in 120 ml tetrahydrofuran was diluted with 80 ml methanol slowly while the solution remained clear. Then 2.0 ml 1.0 N aqueous NaOH was added dropwise. The resulting solution was heated under reflux for about 18 h and monitored by thin layer chromatography until all ester was hydrolyzed. The solvent was evaporated and the residue was triturated with methanol to yield 0.42 g of A salt as a yellow powder. The product was used directly without further purification.

EXAMPLE 2

Response of Hydrogen Peroxide in an Aqueous Sample

Compound A salt (~7 mg) was dissolved in 100 ml 50 mM Tris buffer at pH 7.40. 2.5 ml of this solution was subjected to the scanning of the fluorescence emission spectrum with a spectrofluorometer at an excitation wavelength of 450 nM, as shown by the bottom curve ("♦") in FIG. 1.

Then 20 μL of a solution of horseradish peroxidase (HRP, 2500 unit/ml) was added. The resulting solution was mixed well and then scanned to record a second spectrum, as shown by essentially by the same bottom curve in FIG. 1 ("♦").

Finally, 20 μL of a 5 mM solution of H₂O₂ was added to the compound A and HRP solution. The resulting solution was scanned three times at time intervals 0 ("▲"), 1 ("●") and 2 minutes ("■"), respectively, as shown in FIG. 1.

EXAMPLE 3

Preparation of Lactate Sensor

To a solution of 0.002 g Compound A salt in 0.75 ml de-ionized water were added 0.018 g lactate oxidase, 0.010 g horseradish peroxidase (2500 unit/ml), and 3 g 10% polyvinyl alcohol containing 4% (mole percent) 4-formylstyry N-methylpyridinium acetal (PVA SbQ). The resulting solution was stirred at room temperature for 18 h and then coated onto a polyester film with a 100 μm knife gap.

The coated film was then cured by illuminating the film with a 15 watt UV (365 nm) lamp for 15 min. Then the film was overcoated with a dispersion of 0.3 g of carbon black and 2.7 g of the above-mentioned PVA-SbQ, and the resulting film was then cured in the same way as the first film.

After applying a pressure sensitive adhesive layer in the back of the polyester film, the combined films were punched to produce a 4 mm disc which was assembled into a sensing cartridge, which was then used for measurement with an OPTI® TS instrument (OPTIMedical, Roswell, Ga.) by aspirating through the cartridge solutions having different concentrations of lactate.

Figure 2:
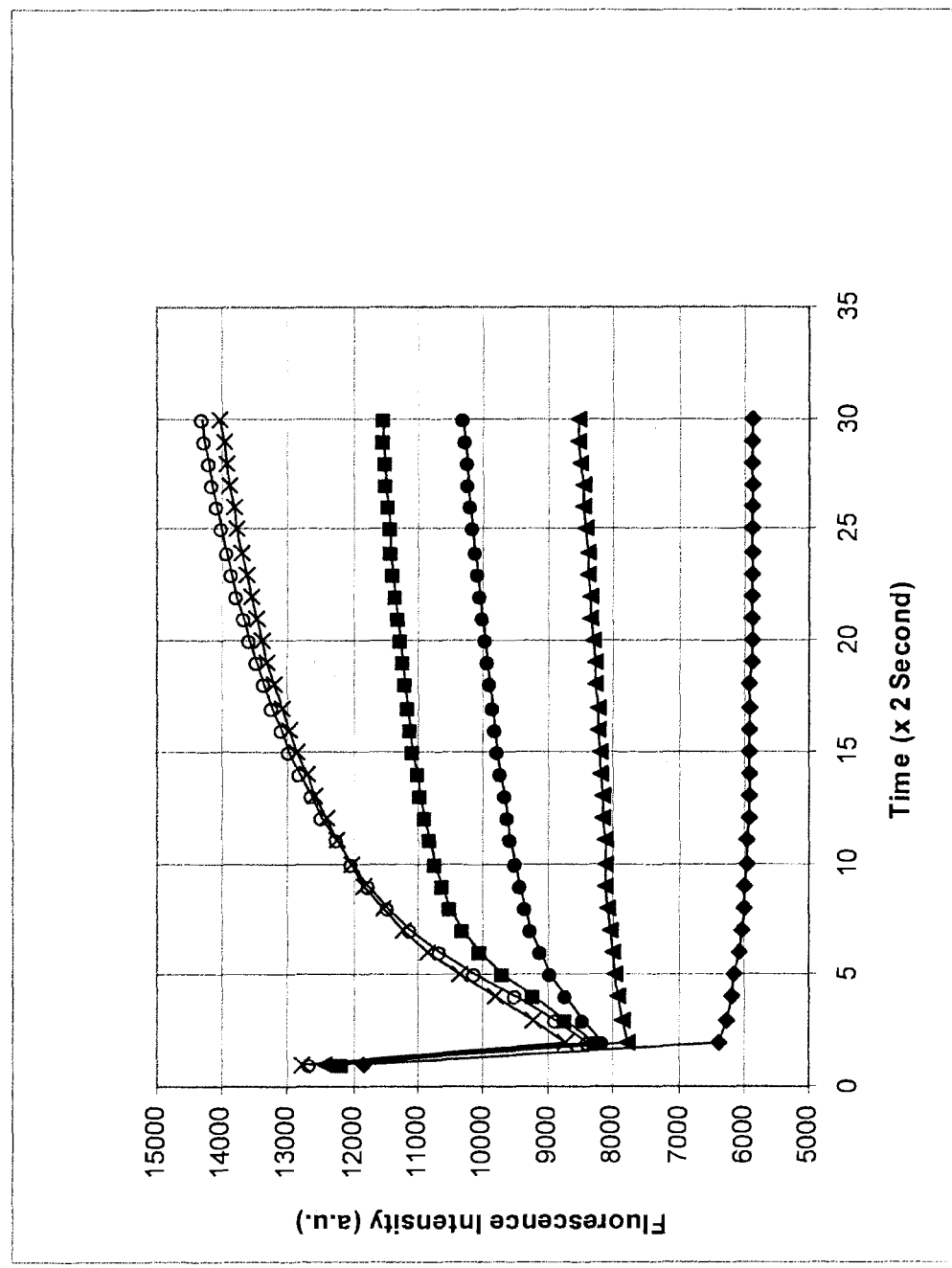
FIG. 2 shows stacked plots of fluorescence emission intensity (arbitrary units "a.u.") versus time obtained by measuring lactate solutions of the following concentrations using a sensor as described in Example 3 below: 0 mM ("♦"); 1 mM ("▲"); 2.5 mM ("●"); 5 mM ("■"); 7.5 mM ("x"); and 15 mM ("○").
Figure 3:
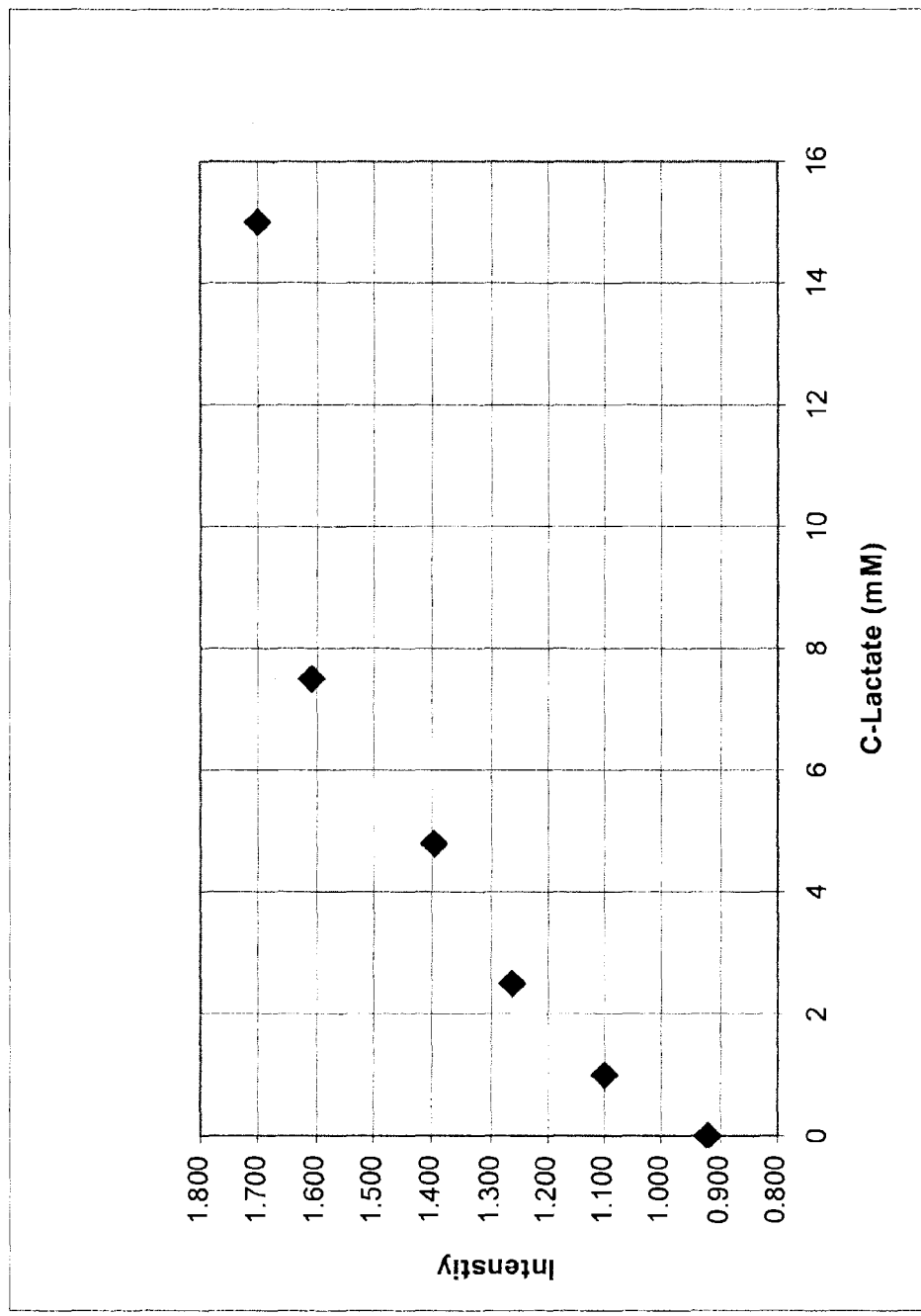
FIG. 3 is a calibration curve for a lactate sensor as described in Example 3 below.

For each solution, the intensity of fluorescence was recorded and plotted as a function of time. The combined results for all of the measurements are shown in FIG. 2 (0 mM lactate ("♦"); 1 mM ("▲"); 2.5 mM ("●"); 5 mM ("■"); 7.5 mM ("x"); and 15 mM ("○")). The results accounted for calibration of the sensor, as shown by the calibration curve (FIG. 3) that was generated by plotting the intensity of fluorescence at 50 second intervals against the concentration of lactate.

EXAMPLE 4

Synthesis of Compound B, a Compound of Formula I

Scheme II below illustrates the overall synthesis of Compound B, which is a compound of Formula I:

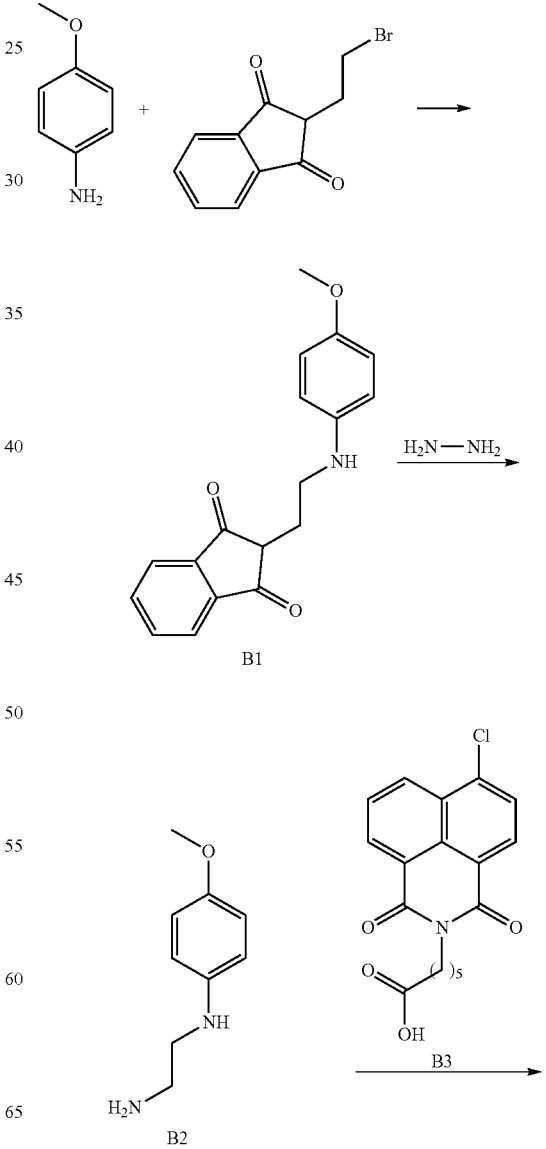

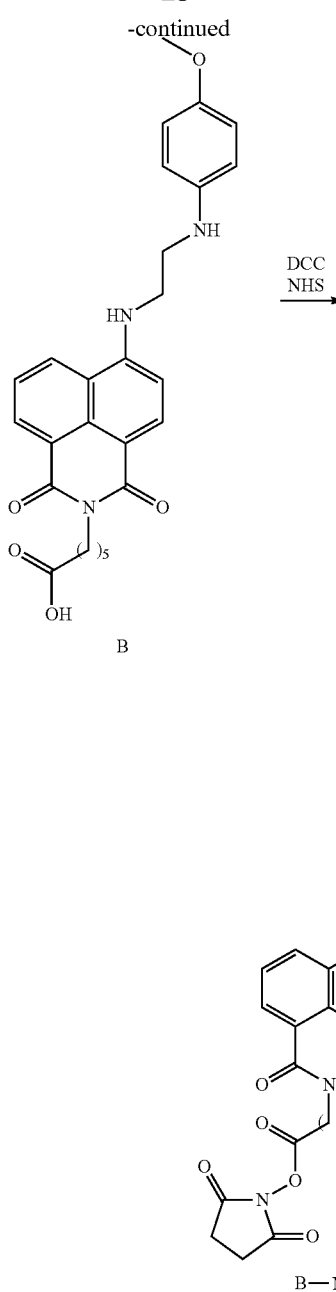

Compound B was obtained as shown in Scheme II above in a four step synthesis. P-anisidine and N-(2-bromoethyl)-phthalimide are commercially available starting materials, and they were reacted to give compound B1. The phthalimide moiety of B1 was cleaved by treating compound B1 with hydrazine monohydrate in boiling ethanol to yield primary amine B2. Compound B2 was reacted with compound B3, which was obtained in a manner analogous to the synthesis of compound A5 described above, to effect chloro substitution by the amino group of B2 to yield product probe B.

The acid moiety of probe B was made amino-reactive in order to attach the probe to a polymeric support containing amino groups. Thus, B was converted into its N-hydroxysuccinimidyl ester B-NHS by reacting B with N-hydroxysuccinimide and N,N'-dicyclohexylcarbodiimide (DCC) in dry DMSO at room temperature to give B-NHS. The resulting solution was used directly in subsequent steps, and B-NHS can be stored as the solution at −18° C. for at least one week.

EXAMPLE 5

Properties and Applications of Compound B

Figure 4:
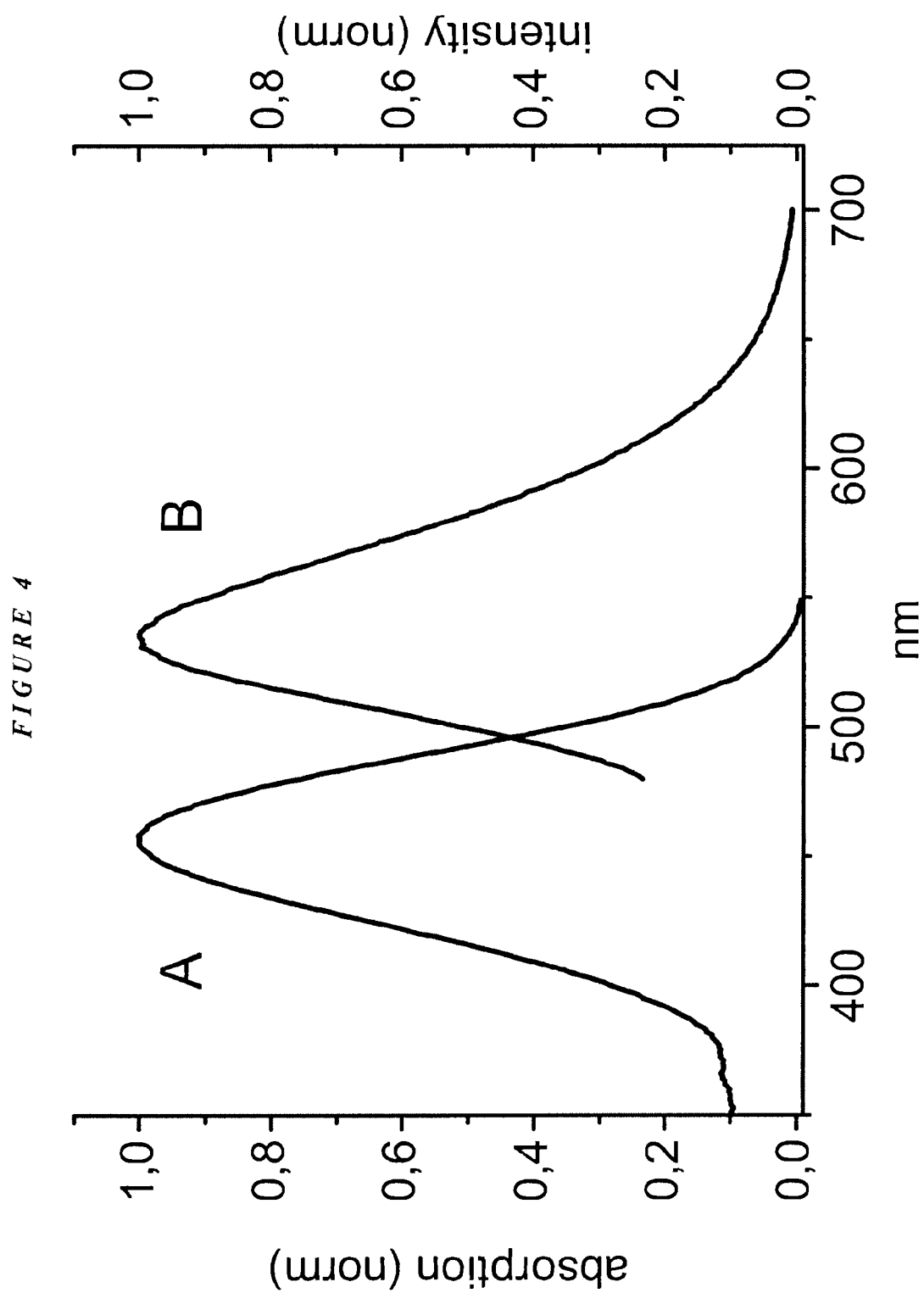
FIG. 4 shows the normalized absorption spectrum (A) and normalized emission spectrum (B) of compound B in phosphate buffer solution (pH 8, 50 mM).

Compound B exhibits an absorption maximum at 455 nm in phosphate buffer solution (pH 8, 50 mM). The molar absorption coefficient $\epsilon$ is $6.0 \times 10^3$ L/mol·cm. Compound B exhibits a yellow fluorescence in aqueous solutions with an emission maximum at 536 nm. FIG. 4 shows the normalized absorption (curve A) and emission spectra (curve B) of compound B.

EXAMPLE 6

Compound B as a PET-Probe for Sensing Hydrogen Peroxide

Figure 5:
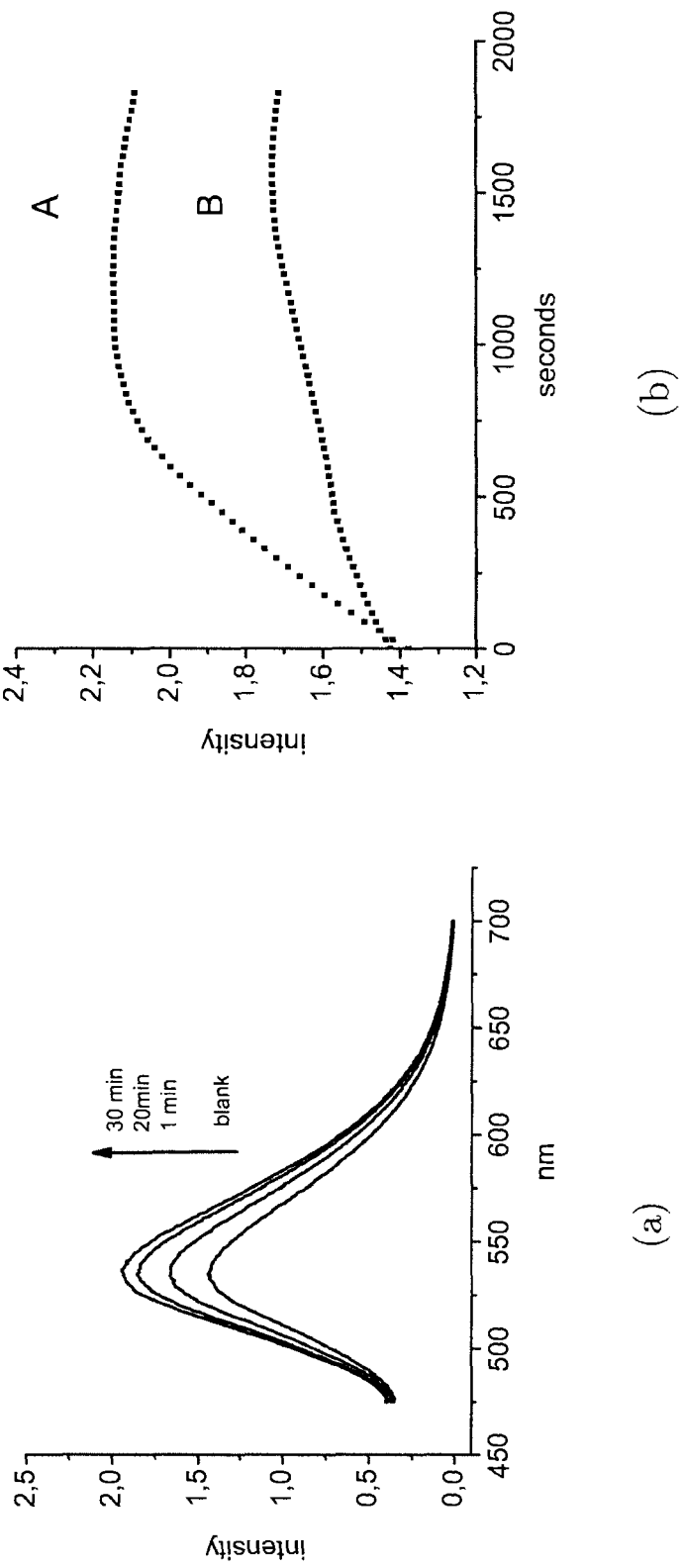
FIG. 5 shows the emission spectra (5a) of compound B (10 μM) with increased fluorescence intensity after the addition of hydrogen peroxide (1 mM) and a time course of fluorescence intensity (5b) at 25° C. in phosphate buffer solution (pH 8, 10 mM) after addition of hydrogen peroxide (1 mM; curve A) and for a blank sample (curve B).

The purpose of this example is to show that compound B can detect hydrogen peroxide. Thus, hydrogen peroxide (1 mM) was combined with compound B (10 μM, 21° C.) in phosphate buffer solution (pH 8, 10 mM) at 25° C. The emission spectra of compound B and the increase in fluorescence intensity was measured at several times within the first 30 minutes of combining compound B with hydrogen peroxide. FIG. 5a shows that fluorescence intensity increased over time, thereby demonstrating the ability of compound B to sense hydrogen peroxide.

Figure 6:
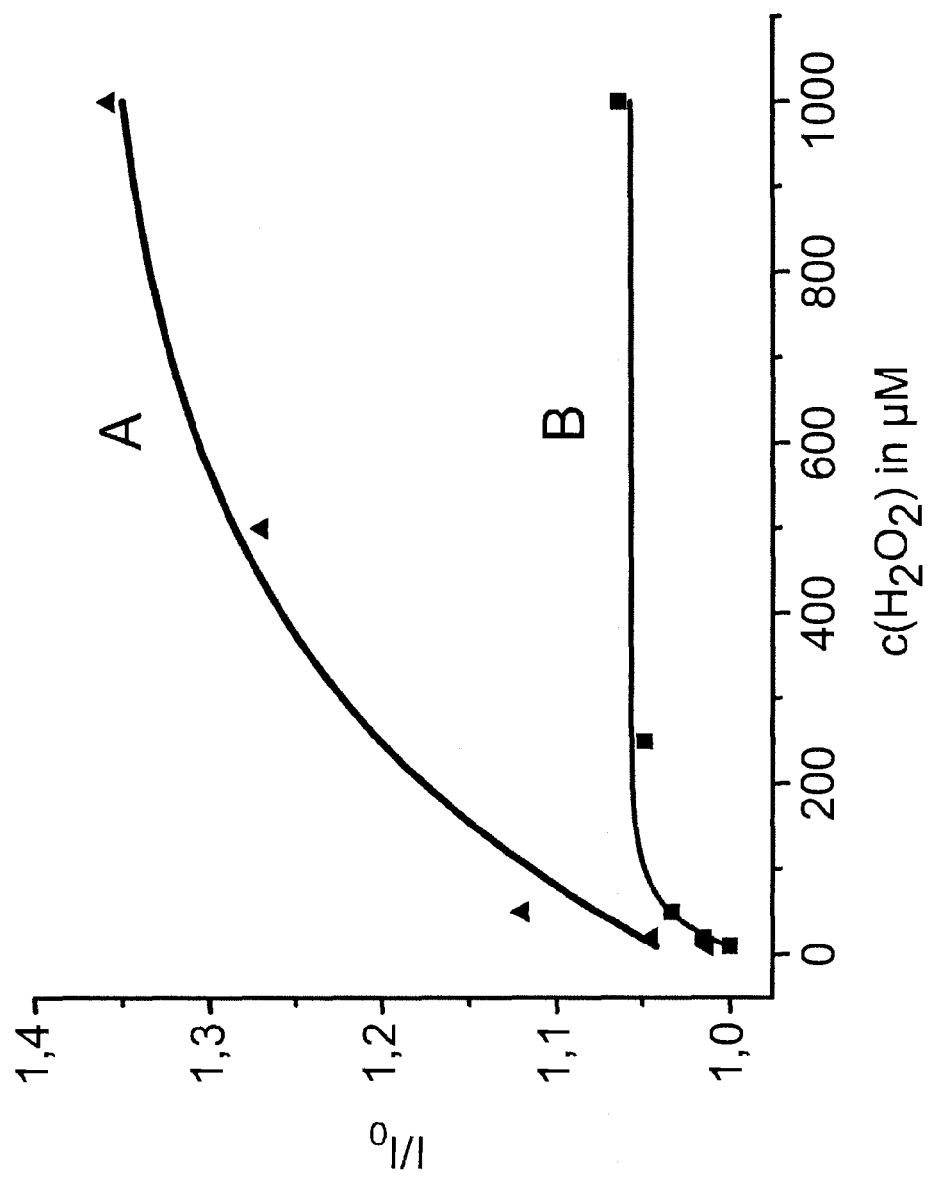
FIG. 6 shows the relative fluorescence intensity ($I/I_0$) of compound B at concentrations 10 μM (curve A) and 5 μM (curve B) in the presence of hydrogen peroxide of various concentrations after 30 minutes.

FIG. 6 depicts results of a time course experiment that shows the time-dependent change of fluorescence intensity of compound B. More specifically, after the addition of hydrogen peroxide as described above, there was observed a linear increase of the fluorescence intensity during the early stages of the reaction (FIG. 5b; curve A). The linear increase ended at about 500 s (8 min.) and the reaction stopped after 1500 s (25 min.) at which point the intensity did not rise any further. Curve B in FIG. 5b shows the growth of the signal of a blank sample containing only compound B in buffer solution. Thus, the time course experiment illustrates a continuous increased in fluorescence intensity and that photobleaching is readily observed after 1500 s (25 min.) and that it occurs both for compound B and a blank sample.

A calibration curve for hydrogen peroxide was established by measuring the fluorescence intensity of compound B in the presence of various concentrations of hydrogen peroxide ranging from 10 μM to 1 mM. in phosphate buffer solution of pH 8 (10 mM), thereby guaranteeing the deprotonation of the amino group. Hence, protonation of the amino receptor was excluded as a factor that would otherwise enhance the background signal of the analyte-free probe.

Fluorescence intensity measurements were measured after 30 minutes of reaction time at 25° C., thereby assuring a fluorescence measurement at its maximum intensity and sensitivity. This is especially important for low analyte concentrations. An acceptable fluorescence measurement can be performed after 600 s (10 min.) for more expedient analytical assays.

FIG. 6 shows two calibration curves of compound B for hydrogen peroxide. They were established by five point calibrations of the relative fluorescence intensity ($I/I_0$). The concentrations of hydrogen peroxide amounted to 10 μM, 20 μM, 50 μM, 250 μM, 500 μM, and 1000 μM, and the concentration of compound B was either 10 μM (curve A; FIG. 6) or 5 μM (curve B, FIG. 6). The calibration curves rise exponentially and they were fitted by Origin with a coefficient of determination ($R^2$) of 0.9 each. FIG. 6 shows that compound B is effective for sensing hydrogen peroxide in the micromolar range. In addition, the calibration curves A and B suggest that a probe concentration of 10 μM is recommended for analytical applications.

EXAMPLE 7

Covalent Attachment of Compound B to a Polymeric Support

The purpose of this example is to demonstrate how compound B is attached to a polymer that is suitable for a hydrogen peroxide sensor, as shown in Scheme III below:

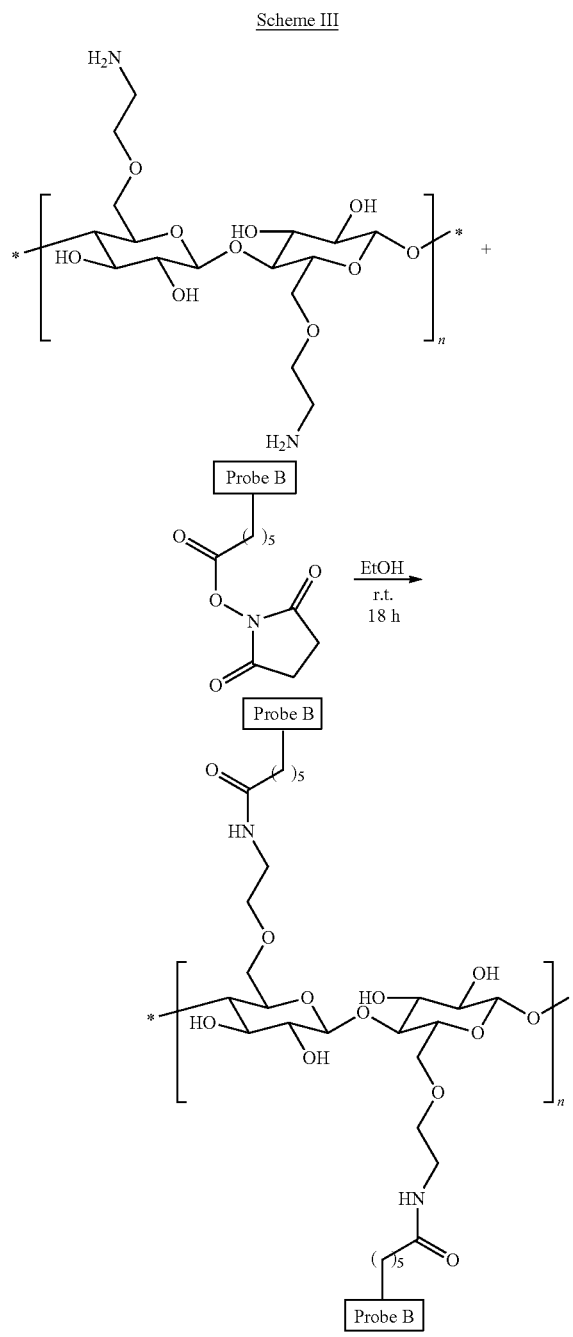

Thus, compound B-NHS was added to an ethanolic suspension of O-(2-aminoethyl)-cellulose, which is an amino polymer. The reaction was carried out overnight and the resultant polymer with attached probe B was collected by centrifugation and then washed several times with ethanol to remove any unbound probe.

A blank sample was prepared in the same manner by combining the non-activated probe, i.e., compound B, not B-NHS, with the amino-modified cellulose, followed by the centrifugation and washing steps. The blank sample showed almost no color whereas the probe-bound cellulose was strongly colored.

EXAMPLE 8

Synthesis of Compound C, a Compound of Formula I

The synthesis of compound C was carried out in five synthetic steps as shown below in Scheme IV:

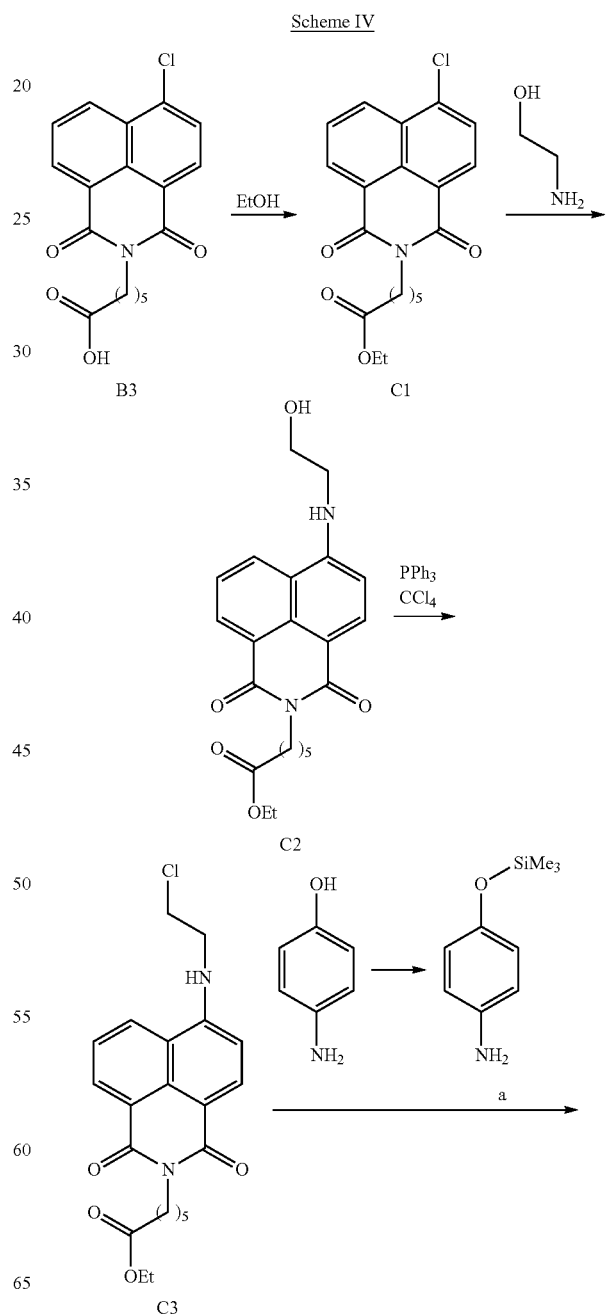

-continued

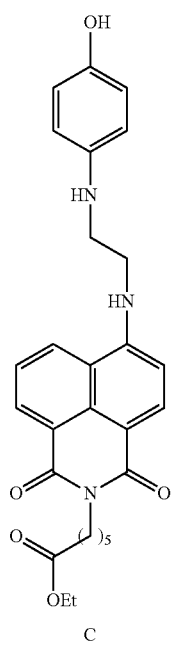

C

Compound B3 described above was esterfied in ethanol to yield compound C1. Treatment of C1 by monoethanolamine effected chloro substitution to yield compound C2. The hydroxyl group of C2 was replaced by a chloro moiety in order to generate an appropriate leaving group in compound C3 via reaction with triphenylphosphine and $CCl_4$ in acetonitrile. In the last step, p-aminophenyl was converted into its TMS-ether, compound a, which was then reacted with compound C3 to yield compound C. The TMS protecting group was cleaved during the final reaction and purification of compound C.

EXAMPLE 9

Properties and Applications of Compound C

Compound C exhibits an absorption maximum at 439 nm in phosphate buffer solution (pH 8, 50 mM). The molar absorption coefficient ε is $5.8 \times 10^3$ L/mol·cm. Compound 13 exhibits a yellow fluorescence in aqueous solutions with an emission maximum at 543 nm. The large Stokes shift of compound C (104 nm) facilitates the separation of exciting and emitting light, thereby reducing the interferences caused by background fluorescence and scattered light.

EXAMPLE 10

Compound C as a PET-Probe for Sensing Hydrogen Peroxide

Figure 7:
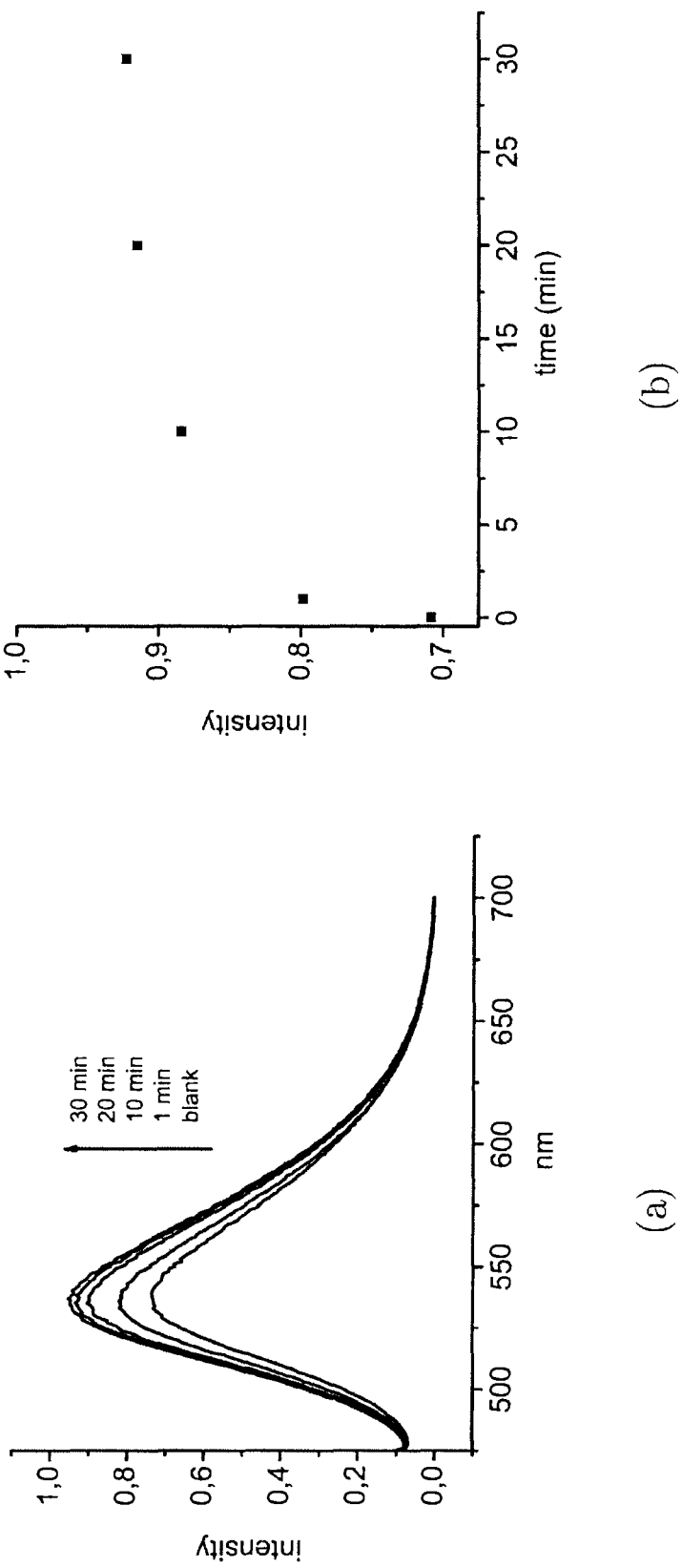
FIG. 7 shows the emission spectra 7(a) of compound C (1 μM) and the increase of fluorescence intensity after the addition of hydrogen peroxide (1 mM) and the time-dependent fluorescence intensity 7(b) in phosphate buffer solution (pH 8, 10 mM) after the addition of hydrogen peroxide (1 mM).

Experiments analogous to those described above for Compound 13 demonstrated that Compound C also is an effective probe for hydrogen peroxide. Thus, compound C (1 mM) and hydrogen peroxide (1 mM) were combined in phosphate buffer solution (phA, 10 mM) at a constant temperature of 25° C. FIG. 7a shows the rise of fluorescence intensity within 30 minutes and FIG. 7b shows the time-course increase of the fluorescence signal at the emission wavelength 530 nm. These measurements show that after 20 minutes the reaction is essentially complete.

Figure 8:
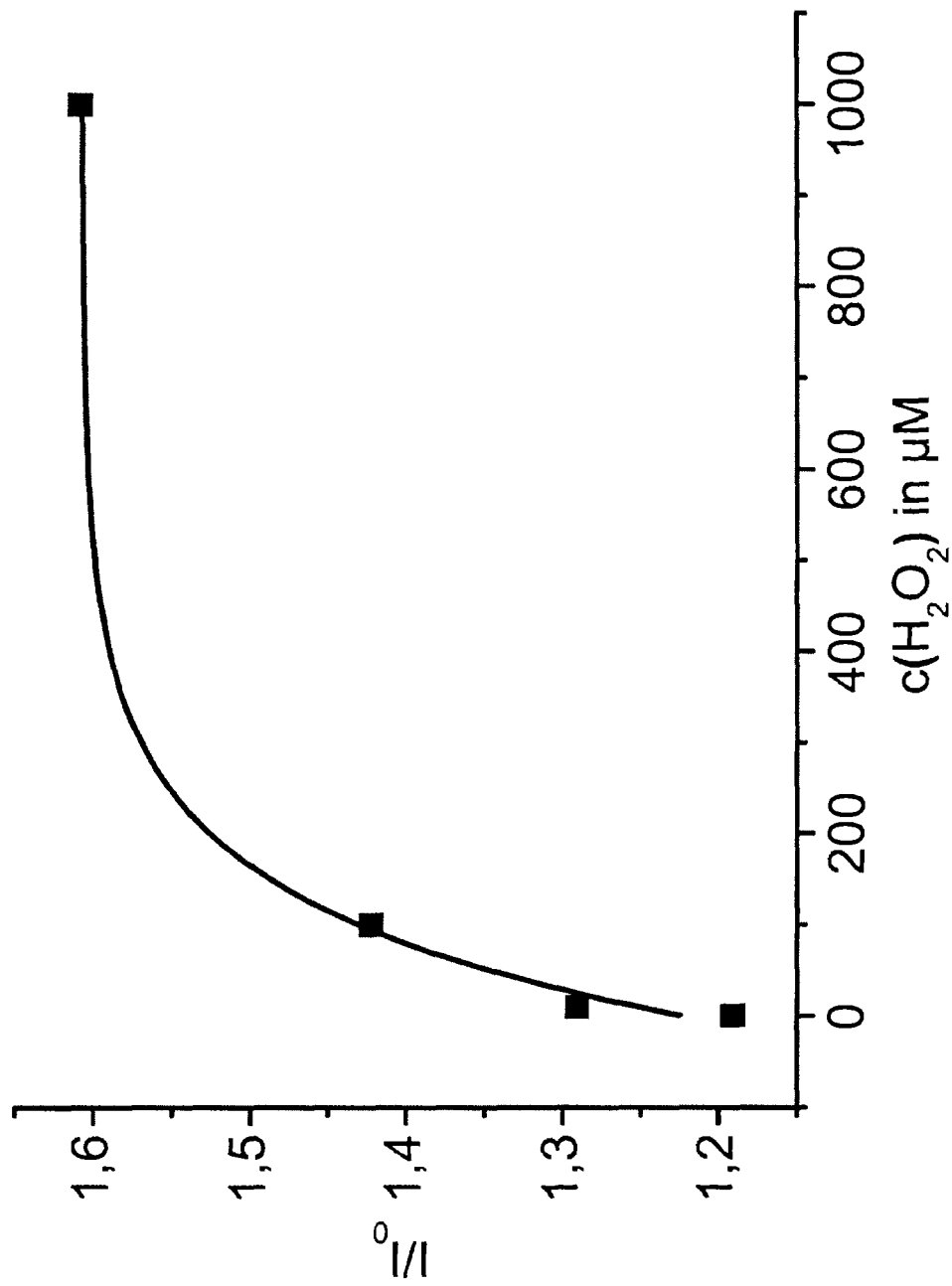
FIG. 8 shows the relative fluorescence intensity ($I/I_0$ of compound C (5 μM) in the presence of hydrogen peroxide of various concentrations after 30 minutes.

A calibration curve of compound C for hydrogen peroxide was established in a manner analogous to that described above for compound 13. FIG. 8 depicts a four point calibration of the relative fluorescence intensity for compound C, corresponding to hydrogen peroxide concentrations of 10 μM, 20 μM, 100 μM, and 1000 μM with compound C present in a concentration of 5 μM.

Using the synthetic methodologies described above, analogous procedures, and adaptations of known organic transformations, a variety of compounds conforming to formulae I and IA are made. Specific examples of these are shown below in Table 2.

TABLE 2

| | Compounds of Formula I/IA: F—L—Q. | | |
|---|---|---|---|
| Example | F | L | Q |
| | 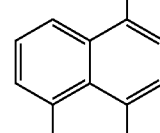 | 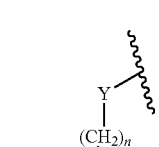 | 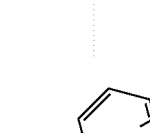 |
| | $R^2$ | X n Y | $R^3$ m |
| 11 | $CH_3CH_2O(CO)(CH_2)_3$— | N 2 N | $OCH_3$ 1 |
| 12 | $(COOH)CH_2$— | N 2 N | $OCH_3$ 1 |
| 13 | $CH_3CH_2O(CO)(CH_2)_5$— | N 2 N | OH 1 |
| 14 | $CH_3CH_2O(CO)(CH_2)_3$— | N 2 O | $OCH_3$ 1 |
| 15 | $(COOH)CH_2$— | N 2 O | $OCH_3$ 1 |
| 16 | $CH_3CH_2O(CO)(CH_2)_5$— | N 2 O | OH 1 |

TABLE 2-continued

Compounds of Formula I/IA: F—L—Q.

| Example | F | L | | | Q | |
|---|---|---|---|---|---|---|
| 17 | $CH_3CH_2O(CO)(CH_2)_3$— | N | 2 | N | $NHCH_3$ | 1 |
| 18 | $(COOH)CH_2$— | N | 2 | N | $NHCH_3$ | 1 |
| 19 | $CH_3CH_2O(CO)(CH_2)_5$— | N | 2 | N | $NH_2$ | 1 |
| 20 | $CH_3CH_2O(CO)(CH_2)_3$— | N | 2 | O | $NHCH_3$ | 1 |
| 21 | $(COOH)CH_2$— | N | 2 | O | $NHCH_3$ | 1 |
| 22 | $CH_3CH_2O(CO)(CH_2)_5$— | N | 2 | O | $NH_2$ | 1 |
| 23 | $CH_3CH_2O(CO)(CH_2)_3$— | N | 3 | N | $OCH_3$ | 1 |
| 24 | $(COOH)CH_2$— | N | 3 | N | $OCH_3$ | 1 |
| 25 | $CH_3CH_2O(CO)(CH_2)_5$— | N | 3 | N | OH | 1 |
| 26 | $CH_3CH_2O(CO)(CH_2)_3$— | N | 3 | O | $OCH_3$ | 1 |
| 27 | $(COOH)CH_2$— | N | 3 | O | $OCH_3$ | 1 |
| 28 | $CH_3CH_2O(CO)(CH_2)_5$— | N | 3 | O | OH | 1 |
| 29 | $CH_3CH_2O(CO)(CH_2)_3$— | N | 3 | N | $NHCH_3$ | 1 |
| 30 | $(COOH)CH_2$— | N | 3 | N | $NHCH_3$ | 1 |
| 31 | $CH_3CH_2O(CO)(CH_2)_5$— | N | 3 | N | $NH_2$ | 1 |
| 32 | $CH_3CH_2O(CO)(CH_2)_3$— | N | 3 | O | $NHCH_3$ | 1 |
| 33 | $(COOH)CH_2$— | N | 3 | O | $NHCH_3$ | 1 |
| 34 | $CH_3CH_2O(CO)(CH_2)_5$— | N | 3 | O | $NH_2$ | 1 |
| 35 | $CH_3CH_2O(CO)(CH_2)_3$— | N | 4 | N | $OCH_3$ | 1 |
| 36 | $(COOH)CH_2$— | N | 4 | N | $OCH_3$ | 1 |
| 37 | $CH_3CH_2O(CO)(CH_2)_5$— | N | 4 | N | OH | 1 |
| 38 | $CH_3CH_2O(CO)(CH_2)_3$— | N | 4 | O | $OCH_3$ | 1 |
| 39 | $(COOH)CH_2$— | N | 4 | O | $OCH_3$ | 1 |
| 40 | $CH_3CH_2O(CO)(CH_2)_5$— | N | 4 | O | OH | 1 |
| 41 | $CH_3CH_2O(CO)(CH_2)_3$— | N | 4 | N | $NHCH_3$ | 1 |
| 42 | $(COOH)CH_2$— | N | 4 | N | $NHCH_3$ | 1 |
| 43 | $CH_3CH_2O(CO)(CH_2)_5$— | N | 4 | N | $NH_2$ | 1 |
| 44 | $CH_3CH_2O(CO)(CH_2)_3$— | N | 4 | O | $NHCH_3$ | 1 |
| 45 | $(COOH)CH_2$— | N | 4 | O | $NHCH_3$ | 1 |
| 46 | $CH_3CH_2O(CO)(CH_2)_5$— | N | 4 | O | $NH_2$ | 1 |
| 47 | $CH_3CH_2O(CO)(CH_2)_3$— | N | 5 | N | $OCH_3$ | 1 |
| 48 | $(COOH)CH_2$— | N | 5 | N | $OCH_3$ | 1 |
| 49 | $CH_3CH_2O(CO)(CH_2)_5$— | N | 5 | N | OH | 1 |
| 50 | $CH_3CH_2O(CO)(CH_2)_3$— | N | 5 | O | $OCH_3$ | 1 |
| 51 | $(COOH)CH_2$— | N | 5 | O | $OCH_3$ | 1 |
| 52 | $CH_3CH_2O(CO)(CH_2)_5$— | N | 5 | O | OH | 1 |
| 53 | $CH_3CH_2O(CO)(CH_2)_3$— | N | 5 | N | $NHCH_3$ | 1 |
| 54 | $(COOH)CH_2$— | N | 5 | N | $NHCH_3$ | 1 |
| 55 | $CH_3CH_2O(CO)(CH_2)_5$— | N | 5 | N | $NH_2$ | 1 |
| 56 | $CH_3CH_2O(CO)(CH_2)_3$— | N | 5 | O | $NHCH_3$ | 1 |
| 57 | $(COOH)CH_2$— | N | 5 | O | $NHCH_3$ | 1 |
| 58 | $CH_3CH_2O(CO)(CH_2)_5$— | N | 5 | O | $NH_2$ | 1 |
| 59 | $CH_3CH_2O(CO)(CH_2)_3$— | N | 6 | N | $OCH_3$ | 1 |
| 60 | $(COOH)CH_2$— | N | 6 | N | $OCH_3$ | 1 |
| 61 | $CH_3CH_2O(CO)(CH_2)_5$— | N | 6 | N | OH | 1 |
| 62 | $CH_3CH_2O(CO)(CH_2)_3$— | N | 6 | O | $OCH_3$ | 1 |
| 63 | $(COOH)CH_2$— | N | 6 | O | $OCH_3$ | 1 |
| 64 | $CH_3CH_2O(CO)(CH_2)_5$— | N | 6 | O | OH | 1 |
| 65 | $CH_3CH_2O(CO)(CH_2)_3$— | N | 6 | N | $NHCH_3$ | 1 |
| 66 | $(COOH)CH_2$— | N | 6 | N | $NHCH_3$ | 1 |
| 67 | $CH_3CH_2O(CO)(CH_2)_5$— | N | 6 | N | $NH_2$ | 1 |
| 68 | $CH_3CH_2O(CO)(CH_2)_3$— | N | 6 | O | $NHCH_3$ | 1 |
| 69 | $(COOH)CH_2$— | N | 6 | O | $NHCH_3$ | 1 |
| 70 | $CH_3CH_2O(CO)(CH_2)_5$— | N | 6 | O | $NH_2$ | 1 |

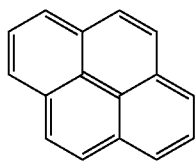 [SMILES: c1cc2ccc3cccc4ccc(c1)c2c34]

| | | X | n | Y | $R^3$ | m |
|---|---|---|---|---|---|---|
| 71 | " | N | 2 | N | $OCH_3$ | 1 |
| 72 | " | N | 2 | N | OH | 1 |
| 73 | " | N | 2 | O | $OCH_3$ | 1 |
| 74 | " | N | 2 | O | OH | 1 |
| 75 | " | N | 2 | N | $NHCH_3$ | 1 |
| 76 | " | N | 2 | N | $NH_2$ | 1 |
| 77 | " | N | 2 | O | $NHCH_3$ | 1 |
| 78 | " | N | 2 | O | $NH_2$ | 1 |
| 79 | " | N | 2 | S | $OCH_3$ | 1 |
| 80 | " | N | 2 | S | OH | 1 |
| 81 | " | N | 2 | S | $NHCH_3$ | 1 |
| 82 | " | N | 2 | S | $NH_2$ | 1 |

TABLE 2-continued

Compounds of Formula I/IA: F—L—Q.

| Example | F | L | | | Q | |
|---|---|---|---|---|---|---|
| 83 | " | N | 3 | N | OCH₃ | 1 |
| 84 | " | N | 3 | N | OH | 1 |
| 85 | " | N | 3 | O | OCH₃ | 1 |
| 86 | " | N | 3 | O | OH | 1 |
| 87 | " | N | 3 | N | NHCH₃ | 1 |
| 88 | " | N | 3 | N | NH₂ | 1 |
| 89 | " | N | 3 | O | NHCH₃ | 1 |
| 90 | " | N | 3 | O | NH₂ | 1 |
| 91 | " | N | 3 | S | OCH₃ | 1 |
| 92 | " | N | 3 | S | OH | 1 |
| 93 | " | N | 3 | S | NHCH₃ | 1 |
| 94 | " | N | 3 | S | NH₂ | 1 |

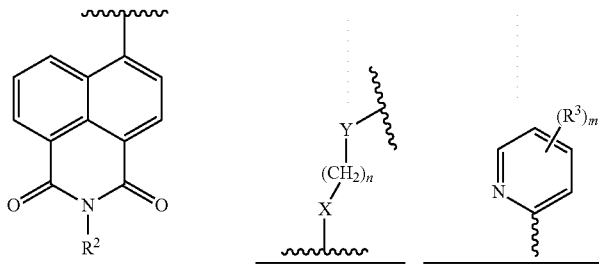

| Example | R² | X | n | Y | R³ | m |
|---|---|---|---|---|---|---|
| 95 | CH₃CH₂O(CO)(CH₂)₃— | N | 2 | N | OCH₃ | 1 |
| 96 | (COOH)CH₂— | N | 2 | N | OCH₃ | 1 |
| 97 | CH₃CH₂O(CO)(CH₂)₅— | N | 2 | N | OH | 1 |
| 98 | CH₃CH₂O(CO)(CH₂)₃— | N | 2 | O | OCH₃ | 1 |
| 99 | (COOH)CH₂— | N | 2 | O | OCH₃ | 1 |
| 100 | CH₃CH₂O(CO)(CH₂)₅— | N | 2 | O | OH | 1 |
| 101 | CH₃CH₂O(CO)(CH₂)₃— | N | 2 | N | NHCH₃ | 1 |
| 102 | (COOH)CH₂— | N | 2 | N | NHCH₃ | 1 |
| 103 | CH₃CH₂O(CO)(CH₂)₅— | N | 2 | N | NH₂ | 1 |
| 104 | CH₃CH₂O(CO)(CH₂)₃— | N | 2 | O | NHCH₃ | 1 |
| 105 | (COOH)CH₂— | N | 2 | O | NHCH₃ | 1 |
| 106 | CH₃CH₂O(CO)(CH₂)₅— | N | 3 | O | NH₂ | 1 |
| 107 | CH₃CH₂O(CO)(CH₂)₃— | N | 3 | N | OCH₃ | 1 |
| 108 | (COOH)CH₂— | N | 3 | N | OCH₃ | 1 |
| 109 | CH₃CH₂O(CO)(CH₂)₅— | N | 3 | N | OH | 1 |
| 110 | CH₃CH₂O(CO)(CH₂)₃— | N | 3 | O | OCH₃ | 1 |
| 111 | (COOH)CH₂— | N | 3 | O | OCH₃ | 1 |
| 112 | CH₃CH₂O(CO)(CH₂)₅— | N | 3 | O | OH | 1 |
| 113 | CH₃CH₂O(CO)(CH₂)₃— | N | 3 | N | NHCH₃ | 1 |
| 114 | (COOH)CH₂— | N | 3 | N | NHCH₃ | 1 |
| 115 | CH₃CH₂O(CO)(CH₂)₅— | N | 3 | N | NH₂ | 1 |
| 116 | CH₃CH₂O(CO)(CH₂)₃— | N | 3 | O | NHCH₃ | 1 |
| 117 | (COOH)CH₂— | N | 3 | O | NHCH₃ | 1 |
| 118 | CH₃CH₂O(CO)(CH₂)₅— | N | 3 | O | NH₂ | 1 |
| 119 | CH₃CH₂O(CO)(CH₂)₃— | N | 4 | N | OCH₃ | 1 |
| 120 | (COOH)CH₂— | N | 4 | N | OCH₃ | 1 |
| 121 | CH₃CH₂O(CO)(CH₂)₅— | N | 4 | N | OH | 1 |
| 122 | CH₃CH₂O(CO)(CH₂)₃— | N | 4 | O | OCH₃ | 1 |
| 123 | (COOH)CH₂— | N | 4 | O | OCH₃ | 1 |
| 124 | CH₃CH₂O(CO)(CH₂)₅— | N | 4 | O | OH | 1 |
| 125 | CH₃CH₂O(CO)(CH₂)₃— | N | 4 | N | NHCH₃ | 1 |
| 126 | (COOH)CH₂— | N | 4 | N | NHCH₃ | 1 |
| 127 | CH₃CH₂O(CO)(CH₂)₅— | N | 4 | N | NH₂ | 1 |
| 128 | CH₃CH₂O(CO)(CH₂)₃— | N | 4 | O | NHCH₃ | 1 |
| 129 | (COOH)CH₂— | N | 4 | O | NHCH₃ | 1 |
| 130 | CH₃CH₂O(CO)(CH₂)₅— | N | 4 | O | NH₂ | 1 |
| 131 | CH₃CH₂O(CO)(CH₂)₃— | N | 5 | N | OCH₃ | 1 |
| 132 | (COOH)CH₂— | N | 5 | N | OCH₃ | 1 |
| 133 | CH₃CH₂O(CO)(CH₂)₅— | N | 5 | N | OH | 1 |
| 134 | CH₃CH₂O(CO)(CH₂)₃— | N | 5 | O | OCH₃ | 1 |
| 135 | (COOH)CH₂— | N | 5 | O | OCH₃ | 1 |
| 136 | CH₃CH₂O(CO)(CH₂)₅— | N | 5 | O | OH | 1 |
| 137 | CH₃CH₂O(CO)(CH₂)₃— | N | 5 | N | NHCH₃ | 1 |

TABLE 2-continued

Compounds of Formula I/IA: F—L—Q.

| Example | F | L | | Q | |
|---|---|---|---|---|---|
| 138 | (COOH)CH$_2$— | N | 5 | N | NHCH$_3$ | 1 |
| 139 | CH$_3$CH$_2$O(CO)(CH$_2$)$_5$— | N | 5 | N | NH$_2$ | 1 |
| 140 | CH$_3$CH$_2$O(CO)(CH$_2$)$_3$— | N | 5 | O | NHCH$_3$ | 1 |
| 141 | (COOH)CH$_2$— | N | 5 | O | NHCH$_3$ | 1 |
| 142 | CH$_3$CH$_2$O(CO)(CH$_2$)$_5$— | N | 5 | O | NH$_2$ | 1 |
| 143 | CH$_3$CH$_2$O(CO)(CH$_2$)$_3$— | N | 6 | N | OCH$_3$ | 1 |
| 144 | (COOH)CH$_2$— | N | 6 | N | OCH$_3$ | 1 |
| 145 | CH$_3$CH$_2$O(CO)(CH$_2$)$_5$— | N | 6 | N | OH | 1 |
| 146 | CH$_3$CH$_2$O(CO)(CH$_2$)$_3$— | N | 6 | O | OCH$_3$ | 1 |
| 147 | (COOH)CH$_2$— | N | 6 | O | OCH$_3$ | 1 |
| 148 | CH$_3$CH$_2$O(CO)(CH$_2$)$_5$— | N | 6 | O | OH | 1 |
| 149 | CH$_3$CH$_2$O(CO)(CH$_2$)$_3$— | N | 6 | N | NHCH$_3$ | 1 |
| 150 | (COOH)CH$_2$— | N | 6 | N | NHCH$_3$ | 1 |
| 151 | CH$_3$CH$_2$O(CO)(CH$_2$)$_5$— | N | 6 | N | NH$_2$ | 1 |
| 152 | CH$_3$CH$_2$O(CO)(CH$_2$)$_3$— | N | 6 | O | NHCH$_3$ | 1 |
| 153 | (COOH)CH$_2$— | N | 6 | O | NHCH$_3$ | 1 |
| 154 | CH$_3$CH$_2$O(CO)(CH$_2$)$_5$— | N | 6 | O | NH$_2$ | 1 |

| | 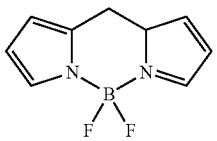 | | | 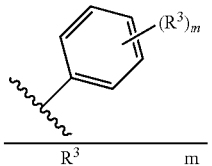 | |
|---|---|---|---|---|---|
| | F | X | n | Y | R$^3$ | m |
| 155 | " | N | 2 | N | OCH$_3$ | 1 |
| 156 | " | N | 2 | N | OH | 1 |
| 157 | " | N | 2 | O | OCH$_3$ | 1 |
| 158 | " | N | 2 | O | OH | 1 |
| 159 | " | N | 2 | N | NHCH$_3$ | 1 |
| 160 | " | N | 2 | N | NH$_2$ | 1 |
| 161 | " | N | 2 | O | NHCH$_3$ | 1 |
| 162 | " | N | 2 | O | NH$_2$ | 1 |
| 163 | " | N | 2 | S | OCH$_3$ | 1 |
| 164 | " | N | 2 | S | OH | 1 |
| 165 | " | N | 2 | S | NHCH$_3$ | 1 |
| 166 | " | N | 2 | S | NH$_2$ | 1 |

| 167 | " | N | 2 | N | OCH$_3$ | 1 |
|---|---|---|---|---|---|---|
| 168 | " | N | 2 | N | OH | 1 |
| 169 | " | N | 2 | O | OCH$_3$ | 1 |
| 170 | " | N | 2 | O | OH | 1 |
| 171 | " | N | 2 | N | NHCH$_3$ | 1 |
| 172 | " | N | 2 | N | NH$_2$ | 1 |
| 173 | " | N | 2 | O | NHCH$_3$ | 1 |
| 174 | " | N | 2 | O | NH$_2$ | 1 |
| 175 | " | N | 2 | S | OCH$_3$ | 1 |
| 176 | " | N | 2 | S | OH | 1 |
| 177 | " | N | 2 | S | NHCH$_3$ | 1 |
| 178 | " | N | 2 | S | NH$_2$ | 1 |

We claim:

1. A compound of formula IA, or a salt thereof:

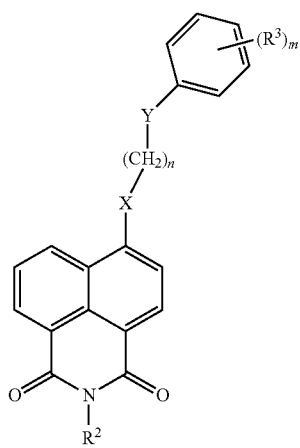

wherein $R^2$ is selected from the group consisting of $C_{1-8}$-alkyl, $C_{1-8}$-alkoxy, $C_{1-8}$-alkyl-aryl, and $C_{1-8}$-alkyl-$C_{1-8}$-alkoxy; wherein any alkyl or aryl is optionally substituted with from one to four —C(O)OR'; wherein each occurrence of R' is independently selected from H, $C_{1-8}$-alkyl and $C_{3-8}$-heterocycloalkyl;

$R^3$, in each instance, is independently selected from the group consisting of $OR^1$, $SR^1$, and $N(R^1)_2$;

$R^1$ is hydrogen or unsubstituted $C_{1-6}$-alkyl;

X and Y are independently selected from group consisting of —$NR^1$—, —O—, and —S—;

m is 1, 2, 3, 4, or 5;

n is 1, 2, 3, 4, 5, or 6; and wherein when n is at least 2, then 2 and 4 hydrogen atoms in adjacent —$CH_2$— groups in —X—$(CH_2)_n$Y— are optionally not present so as to represent the moieties —CH=CH— and respectively.

2. The compound of claim 1 in which:

$R^2$ is $C_{1-8}$-alkyl, or $C_{1-8}$-alkyl-aryl;

X and Y are independently selected from the group consisting of —NH— and —O—;

m is 1, 2, or 3; and n is 2.

3. The compound of claim 1 which is selected from the group consisting of:

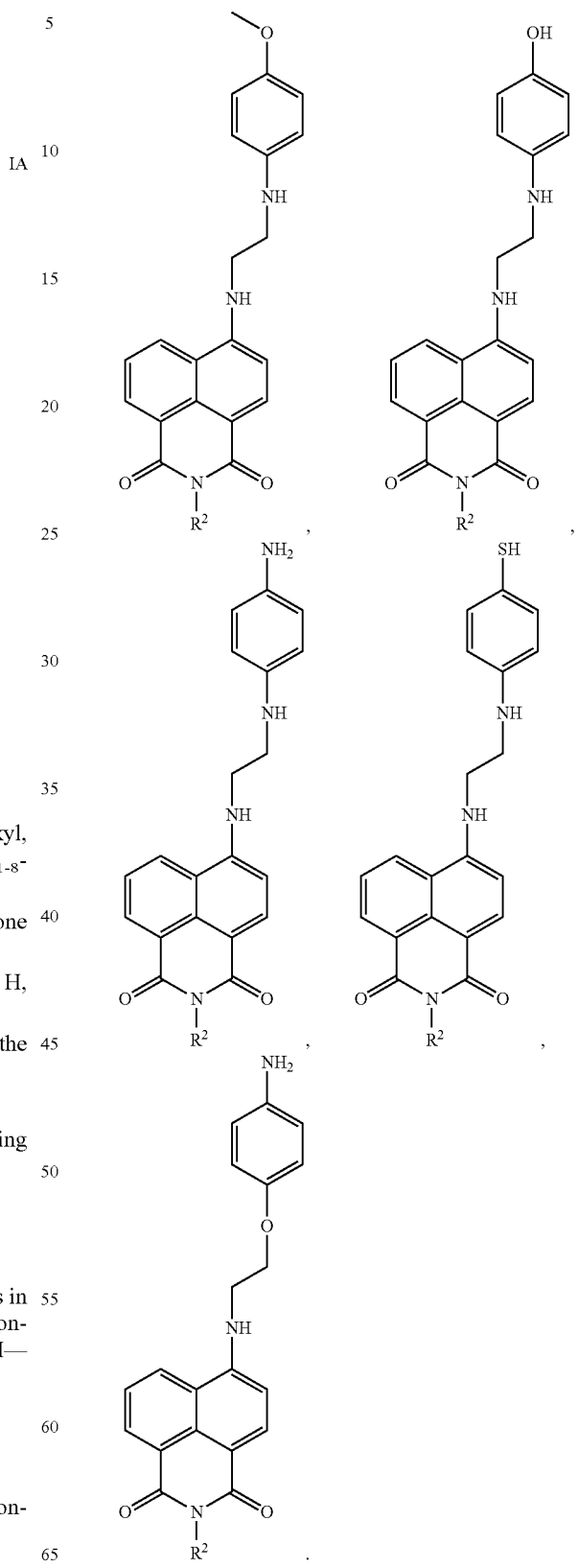

4. The compound of claim 3 which is selected from the group consisting of:
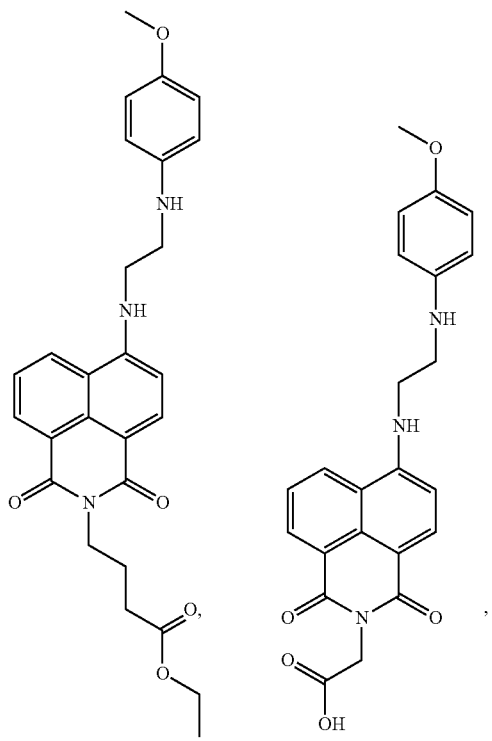
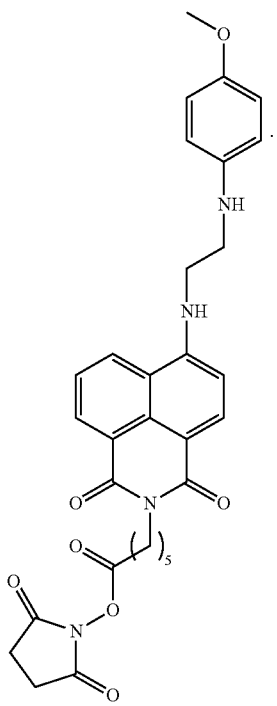
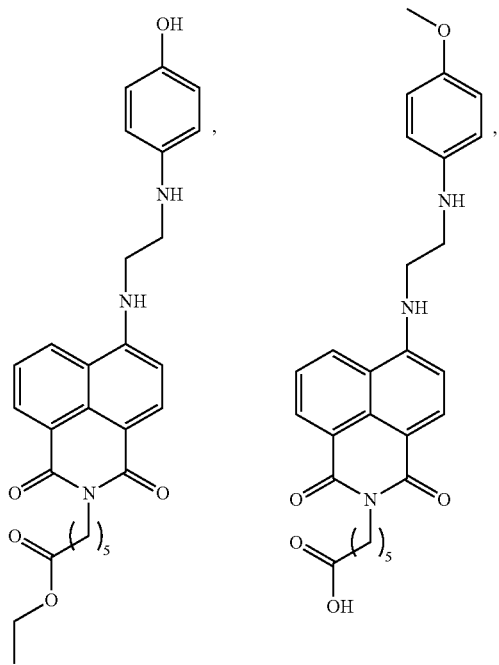
-continued
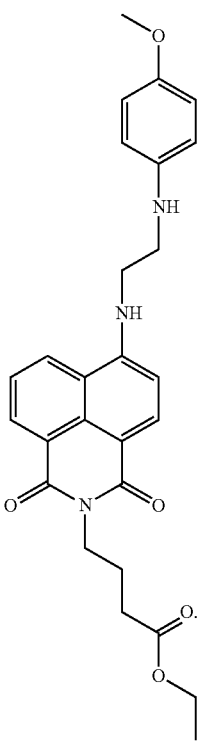 [SMILES: CCOC(=O)CCCN1C(=O)c2cccc3c(NCCNc4ccc(OC)cc4)ccc(c23)C1=O]
5. The compound of claim 4 which is:

6. The compound of claim 4 which is:

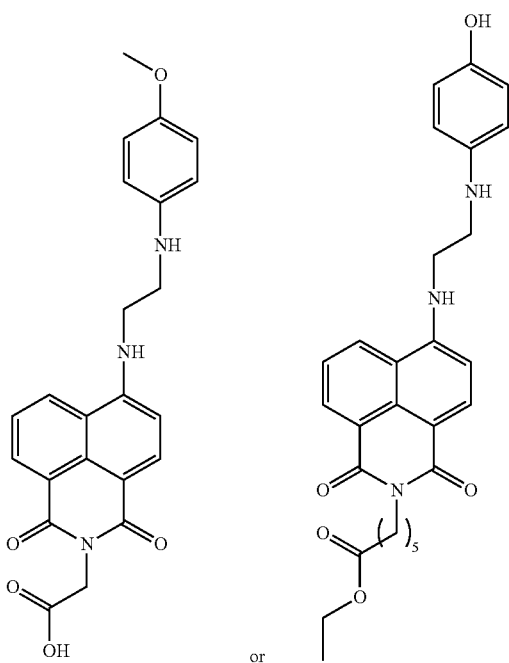

7. A method of determining a concentration of hydrogen peroxide in a sample comprising:
(a) contacting a sample suspected of containing hydrogen peroxide ($H_2O_2$) with a sufficient amount of a compound of formula IA or a salt thereof:

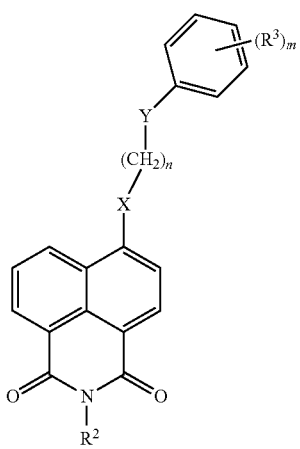

IA wherein
$R^2$ is selected from the group consisting of $C_{1-8}$-alkyl, $C_{1-8}$-alkoxy, $C_{1-8}$-alkyl-aryl, and $C_{1-8}$-alkyl-$C_{1-8}$-alkoxy; wherein
any alkyl or aryl is optionally substituted with from one to four —C(O)OR'; wherein
each occurrence of R' is independently selected from H, $C_{1-8}$-alkyl and $C_{3-8}$-heterocycloalkyl;
$R^3$, in each instance, is independently selected from the group consisting of $OR^1$, $SR^1$, and $N(R^1)_2$;
$R^1$ is hydrogen or unsubstituted $C_{1-6}$-alkyl;
X and Y are independently selected from group consisting of —$NR^1$—, —O—, and —S—;
m is 1, 2, 3, 4, or 5;
n is 1, 2, 3, 4, 5, or 6; and
wherein when n is at least 2, then 2 and 4 hydrogen atoms in adjacent —$CH_2$— groups in —X—$(CH_2)_n$Y— are optionally not present so as to represent the moieties —CH=CH— and —C≡C—, respectively;
(b) irradiating the sample with energy in the form of electromagnetic radiation, including energy at an excitation wavelength at which the fluorophore absorbs the energy;
(c) measuring an intensity of energy emitted from the irradiated sample at an emission wavelength, if any; and
(d) correlating the measured intensity of the emitted energy with a concentration of the hydrogen peroxide in the sample.

8. A method of detecting the presence of hydrogen peroxide in a sample comprising:
(a) contacting a sample suspected of containing hydrogen peroxide with a sufficient amount of a compound of formula IA or a salt thereof:

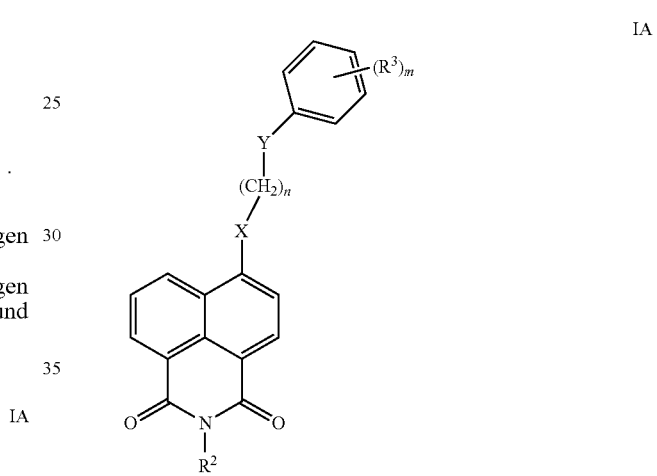

IA wherein
$R^2$ is selected from the group consisting of $C_{1-8}$-alkyl, $C_{1-8}$-alkoxy, $C_{1-8}$-alkyl-aryl, and $C_{1-8}$-alkyl-$C_{1-8}$-alkoxy; wherein
any alkyl or aryl is optionally substituted with from one to four —C(O)OR'; wherein
each occurrence of R' is independently selected from H, $C_{1-8}$-alkyl and $C_{3-8}$-heterocycloalkyl;
$R^3$, in each instance, is independently selected from the group consisting of $OR^1$, $SR^1$, and $N(R^1)_2$;
$R^1$ is hydrogen or unsubstituted $C_{1-6}$-alkyl;
X and Y are independently selected from group consisting of —$NR^1$—, —O—, and —S—;
m is 1, 2, 3, 4, or 5;
n is 1, 2, 3, 4, 5, or 6; and
wherein when n is at least 2, then 2 and 4 hydrogen atoms in adjacent —$CH_2$— groups in —X—$(CH_2)_n$Y— are optionally not present so as to represent the moieties —CH=CH— and —C≡C—, respectively;
(b) irradiating the sample with energy in the form of electromagnetic radiation, including energy at an excitation wavelength at which the fluorophore absorbs the energy;
(c) detecting energy emitted from the irradiated sample at an emission wavelength, if any;
wherein the detection of emitted energy in step (c) supports a conclusion that at least some hydrogen peroxide is present in the sample.

9. The method of claim 8 which further comprises measuring an intensity of the emitted energy at the emission wavelength.

* * * * *